US011786481B2

(12) United States Patent
Tsai et al.

(10) Patent No.: US 11,786,481 B2
(45) Date of Patent: *Oct. 17, 2023

(54) FORMULATION AND PROCESS FOR MODULATING WOUND HEALING

(71) Applicant: BioMendics, LLC, Fairlawn, OH (US)

(72) Inventors: Chun-che Tsai, Kent, OH (US); Karen M. McGuire, Akron, OH (US); James M. Jamison, Cleveland Heights, OH (US); Jack L. Summers, Sun City Center, FL (US)

(73) Assignee: BioMendics, LLC, Fairlawn, OH (US)

( * ) Notice: Subject to any disclaimer, the term of this patent is extended or adjusted under 35 U.S.C. 154(b) by 10 days.

This patent is subject to a terminal disclaimer.

(21) Appl. No.: 17/221,181

(22) Filed: Apr. 2, 2021

(65) Prior Publication Data
US 2021/0228501 A1 Jul. 29, 2021

Related U.S. Application Data

(63) Continuation of application No. 16/584,195, filed on Sep. 26, 2019, now abandoned, which is a
(Continued)

(51) Int. Cl.
A61K 31/05 (2006.01)
A61K 31/085 (2006.01)
(Continued)

(52) U.S. Cl.
CPC ............ A61K 31/05 (2013.01); A61K 8/33 (2013.01); A61K 8/347 (2013.01); A61K 8/602 (2013.01);
(Continued)

(58) Field of Classification Search
CPC .................................. A61K 31/05
See application file for complete search history.

(56) References Cited

U.S. PATENT DOCUMENTS 5,498,795 A 3/1996 Song et al.
6,008,260 A 12/1999 Pezzuto et al.
(Continued)

FOREIGN PATENT DOCUMENTS

CN 101991590 A 3/2011
EP 0816329 1/1998
(Continued)

OTHER PUBLICATIONS

Lee et al., "A role for the NAD-dependent deacetylase Sirt1 in the regulation of autophagy", PNAS, 2008, vol. 105, No. 9, pp. 3374-3379.
(Continued)

Primary Examiner — Benjamin J Packard
(74) Attorney, Agent, or Firm — MacMillan, Sobanski & Todd, LLC

(57) ABSTRACT

Methods and compounds are disclosed for wound healing by modulating autophagy. A formulation for modulating autophagy comprises a first modulating compound (FAM) selected from compounds having the general structure (I):

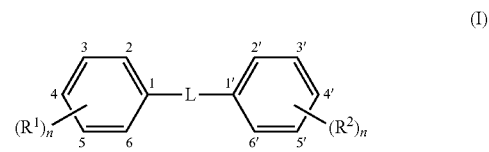

wherein: L represents a linker selected from —C≡C—, (a tolan), —CH=CH— (a stilbene, preferably trans); or —CR$_a$=CR$_b$— a stilbene derivative; where R$_a$ and R$_b$ are independently H or phenyl optionally substituted with —(R$^3$)$_p$ or —(R$^4$)$_q$;
(Continued)

$R^1$ to $R^4$ are independent substituents at any available position of the phenyl rings, preferably at 3, 3', 4, 4', and/or 5, 5'; and m, n, p, and q are independently 0, 1, 2, or 3 representing the number of substituents of the rings, respectively, but at least one of m or n must be ≥1. Each $R^1$ to $R^2$ is independently selected from substituents described herein, including but not limited to hydroxyl, alkoxy, halo, halomethyl and glycosides. The formulation may also include an auxiliary autophagy modulating compound (AAM) as described herein. The formulation may include a hydrogel formed by the compounds themselves or otherwise and may include salts and/or complexes.

23 Claims, 6 Drawing Sheets

Related U.S. Application Data continuation of application No. 16/058,437, filed on Aug. 8, 2018, now Pat. No. 10,426,742, which is a continuation of application No. 15/093,146, filed on Apr. 7, 2016, now Pat. No. 10,045,950.

(60) Provisional application No. 62/144,539, filed on Apr. 8, 2015.

(51) Int. Cl.

| | | |
|---|---|---|
| *A61K 31/09* | (2006.01) | |
| *A61K 31/7034* | (2006.01) | |
| *A61K 45/06* | (2006.01) | |
| *A61K 9/06* | (2006.01) | |
| *A61K 47/36* | (2006.01) | |
| *A61K 47/40* | (2006.01) | |
| *A61Q 19/08* | (2006.01) | |
| *A61Q 7/00* | (2006.01) | |
| *A61K 8/34* | (2006.01) | |
| *A61K 8/33* | (2006.01) | |
| *A61K 8/60* | (2006.01) | |
| *A61K 8/73* | (2006.01) | |
| *A61K 8/67* | (2006.01) | |
| *A61K 9/00* | (2006.01) | |
| *A61K 9/08* | (2006.01) | |
| *A61K 9/19* | (2006.01) | |
| *A61K 8/70* | (2006.01) | |
| *A61K 31/03* | (2006.01) | |
| *A61K 31/167* | (2006.01) | |
| *A61K 31/375* | (2006.01) | |
| *A61K 31/655* | (2006.01) | |

(52) U.S. Cl.
CPC ............... *A61K 8/676* (2013.01); *A61K 8/70* (2013.01); *A61K 8/733* (2013.01); *A61K 8/738* (2013.01); *A61K 9/0019* (2013.01); *A61K 9/06* (2013.01); *A61K 9/08* (2013.01); *A61K 9/19* (2013.01); *A61K 31/03* (2013.01); *A61K 31/085* (2013.01); *A61K 31/09* (2013.01); *A61K 31/167* (2013.01); *A61K 31/375* (2013.01); *A61K 31/655* (2013.01); *A61K 31/7034* (2013.01); *A61K 45/06* (2013.01); *A61K 47/36* (2013.01); *A61K 47/40* (2013.01); *A61Q 7/00* (2013.01); *A61Q 19/08* (2013.01); *Y02A 50/30* (2018.01)

(56) References Cited

U.S. PATENT DOCUMENTS

| | | | |
|---|---|---|---|
| 6,197,834 B1 | 3/2001 | Docherty | |
| 6,355,692 B2 | 3/2002 | Docherty | |
| 6,599,945 B2 | 7/2003 | Docherty et al. | |
| 7,094,809 B2 | 8/2006 | Docherty et al. | |
| 7,321,050 B2 | 1/2008 | Chen et al. | |
| 7,678,819 B2 | 3/2010 | Kung et al. | |
| 7,868,047 B2 | 1/2011 | Chen et al. | |
| 8,017,634 B2 | 9/2011 | Sinclair et al. | |
| 8,680,142 B2 | 3/2014 | Tsai et al. | |
| 8,716,355 B2 | 5/2014 | Tsai | |
| 8,822,382 B2 * | 9/2014 | Mir ........................ | A01N 25/22 |
| | | | 504/147 |
| 9,464,033 B2 | 10/2016 | Scott et al. | |
| 2005/0059733 A1 | 3/2005 | Chen et al. | |
| 2006/0084135 A1 | 4/2006 | Howitz et al. | |
| 2008/0139666 A1 | 6/2008 | Chen et al. | |
| 2011/0130468 A1 | 6/2011 | Tsai | |
| 2011/0136751 A1 | 6/2011 | Estrela et al. | |
| 2011/0160301 A1 | 6/2011 | Tsai et al. | |
| 2012/0058088 A1 | 3/2012 | Sardi | |
| 2012/0070401 A1 | 3/2012 | Zhang et al. | |

FOREIGN PATENT DOCUMENTS

| | | | |
|---|---|---|---|
| WO | 2007020673 A1 | 2/2007 | |
| WO | 2009126700 A1 | 10/2009 | |
| WO | 2011097347 A2 | 8/2011 | |
| WO | 2013134415 A1 | 9/2013 | |
| WO | 2014074765 A2 | 5/2014 | |
| WO | 2016032925 A1 | 3/2016 | |

OTHER PUBLICATIONS

Soder, "Pursuing a cancer cure", Crain's Cleveland Business, 2009.
Amaravadi et al., "Principles and Current Strategies for Targeting Autophagy for Cancer Treatment", Clinical Cancer Research, 2011, vol. 17, No. 4, pp. 654-666.
Sanna et al., "Development of novel cationic chitosan- and anionic alginate-coated poly(D,L-lactide-co-glycolide) nanoparticles for controlled release and light protection of resveratrol", International Journal of Nanomedicine, 2012, vol. 7, pp. 5501-5516.
Lee, et al., "Alginate: properties and biomedical applications", Progress in Polymer Science, 2012, vol. 37, No. 1, pp. 106-126.
Moores et al., "Vitamin C: a wound healing perspective", British Journal of Community Nursing, 2013, vol. 18, No. 12, pp. S6, S8-S11.
McGuire et al., "Synergistic Antitumor Activity of Vitamin C and K3 on Human Bladder Cancer Cell Lines", Journal of Cancer Therapy, 2013, vol. 4, pp. 7-19.
Pinho, et al., "Cyclodextrin-based hydrogels toward improved wound dressings", Critical Reviews in Biotechnology, 2014, vol. 34, No. 4, pp. 328-337.
Alayev et al., "Effects of Combining Rapamycin and Resveratrol on Apoptosis and Growth of TSC2-Deficient Xenograft Tumors", American Journal of Respiratory Cell and Molecular Biology, 2015, vol. 53, No. 5, pp. 637-646.
Japanese Patent Office, Examiner's Decision of Refusal for Japanese application No. 2017-553168, dated Sep. 30, 2020.
PCT International Search Report and Written Opinion, Application No. PCT/US2016/026355, dated Sep. 28, 2016.
Intellectual Property Office of Singapore, Written Opinion, Application No. 11201707919Q, dated Oct. 18, 2018.
Extended European Search Report, Application No. 16777246.6, dated Mar. 4, 2019.
Indian Office Action, Application No. 201747038805, dated Dec. 19, 2019.
Japanese Office Action, Application No. 2017-553168, dated Dec. 24, 2019.
Intellectual Property Office of Singapore Written Opinion, Application No. 11201707919Q, dated Mar. 11, 2020.

(56) References Cited

OTHER PUBLICATIONS

Australian Examination report No. 1 for standard patent application, Application No. 2016246616, dated Jun. 22, 2020.
Australian Examination report No. 2 for Australian application No. 2016246616, dated Dec. 3, 2020.
Chinese First Office Action, Application No. 201680023068.9, dated Mar. 19, 2020.
Brazilian Pre-Examination Office Action for Brazilian application No. 112017021271-4, dated Jan. 7, 2021.
Intellectual Property Office of Singapore Examination Report, Application No. 11201707919Q, dated Nov. 29, 2021.
Intellectual Property Corporation of Malaysia Substantive Examination Adverse Report, Application No. PI 2017703652, dated Oct. 11, 2021.
Canadian Examination Report, Application No. 2,982,161, dated Apr. 21, 2022.
Japanese First Office Action, Application No. 2021-014601, dated Jan. 13, 2022.

* cited by examiner

FORMULATION AND PROCESS FOR MODULATING WOUND HEALING

This application is a continuation application of U.S. application Ser. No. 16/584,195, filed under 35 U.S.C. § 111(a) on Sep. 26, 2019, published; which is a continuation application of U.S. application Ser. No. 16/058,437, filed under 35 U.S.C. § 111(a) on Aug. 8, 2018, issued as U.S. Pat. No. 10,426,742; which is a continuation application of U.S. application Ser. No. 15/093,146, filed under 35 U.S.C. § 111(a) on Apr. 7, 2016, issued as U.S. Pat. No. 10,045,950; which claims priority to U.S. Provisional Application No. 62/144,539, filed under 35 U.S.C. § 111(b) on Apr. 8, 2015. The entire disclosures of all the aforementioned applications are expressly incorporated herein by reference for all purposes.

BACKGROUND OF THE INVENTION

The present invention relates generally to the field of cellular biology and, more particularly, to compounds, formulations, and methods for modulating autophagy to treat a wound or skin related disease or condition. The name, "autophagy," also known as autophagocytosis, is derived from the Greek words meaning "eat" and "self." Autophagy is generally defined as self-digestion.

Autophagy is primarily a lysosomal salvage or recycling pathway that is commonly used by cells to perform homeostatic functions by degrading aging proteins and organelles and reabsorbing nucleotides, amino acids, and free fatty acids for new molecule synthesis and ATP production. Autophagy may be up-regulated in response to extra- or intracellular stress and signals such as starvation, growth factor deprivation, ER stress, and pathogen infection as a cellular-level self-preservation mechanism. In some pathologic conditions, it may be desirable to stimulate the autophagy process, while in other pathologic conditions, such as wound healing, it may be desirable to suppress or slow the autophagy process to reduce the destruction of cells. Thus, modulation of autophagy may invoke either enhancing/stimulating or suppressing/slowing the cell growth and cell death process.

The most common form of autophagy involves (1) the formation of an isolation membrane, which extends and the termini ultimately (2) fuse to encompass the cellular contents within a double-membrane vesicle known as an autophagosome. The autophagosome then (3) fuses with a lysosome that provides enzymes to (4) digest the contents of the autophagosome, which contents then become available to the cell again as raw materials or building block nutrients. Autophagy exhibits some similarities to the parallel proteasome degradation of ubiquitin-tagged proteins, but differs in that the autophagosome contains not only proteins, but also cytoplasm, mitochondria, organelles and other cellular structures. In this sense it is known as a bulk degradation system.

Since the process of autophagy can be both beneficial and detrimental to the cell depending on external factors and conditions, the process must be tightly regulated. Both yeast and mammalian systems have been studied and utilize up to 36 proteins. FIG. 1 illustrates the process in mammals.

The yeast autophagy-related gene product (Atg8) has three mammalian homologues: (1) LC3, (2) GABAA receptor-associated protein (GABARAP), and (3) Golgi-associated ATPase enhancer (GATE-16). Among them, LC3 is most actively studied and frequently used as a mammalian autophagy marker. Shortly after translation (proLC3), LC3 is processed at the C-terminus by Atg4A or Atg4B into LC3-I. Upon induction or enhancement of autophagy, LC3-I is conjugated to the substrate phosphatidylethanolamine (PE) via E1 (yeast Atg7) and E2 (yeast Atg3). The PE-LC3-I conjugate is referred to as LC3-II. This conjugation occurs in the process at the point of autophagosome formation and leads to the conversion of soluble LC3-I to the autophagic vesicle associated LC3-II. This lipid conjugation allows LC3-II to be used as a marker of autophagy activity.

Wound progression is caused by many mechanisms including local tissue hypo-perfusion, prolonged inflammation, free radical damage, apoptosis, and necrosis. These are typically broken up into three stages following the injury including; (i) the inflammation phase, (ii) cell proliferation phase and (iii) remodeling phase. Each one of these phases is linked to a biologically and histologically unique fingerprint and autophagy plays a special role at each phase. For example, during the inflammation stage, autophagy is initially protective of tissue in that it attempts to keep the wound edge cells from dying. In the proliferative stage, during which involves cell multiplication and migration of multiple cell types to close the wound, autophagy helps to regulate β1-integrins and other cell migration proteins to form a controlled line of cells at the leading edge of the wound. In remodeling, the direction of these migrating cells is often controlled by the directionality and deposition of collagen that is secreted by these transformed fibroblasts as pro-collagen. Collagen along with other components such as fibronectin and lamin help regenerate the basement membrane during the proliferation and migration stages.

During the wound healing process collagen fibrils provide the structural topology, rigidity and organization that allows for proper cell migration. In chronic wounds and burns this environment is subjected to a variety of factors including an altered pH, chronic inflammation and often a loss in the basement membrane including the essential collagen tracts that are used by migrating wound cells (e.g. keratinocytes, fibroblasts, myofibroblasts) to fill the wound and restore a layer of intact skin to protect the body from invading microbes and environmental factors (e.g. temperature regulation). During the natural healing process skin cells secrete the soluble form of collagen known as pro-collagen that can form higher order structures enzymatically or undergo an entropy driven self-assembly process (Prockop, D. and D. Hulmes (1994). Pro-collagen is secreted from the cell as a triple helix, which can self-assemble into fibrils due to its liquid crystal nature. This process is highly dependent on the pH, ionic strength, temperature, and concentration. Fibrils then are formed into individual collagen fibers, which are randomly assembled into higher order 3-dimensional networks and structures.

U.S. Pat. Nos. 6,599,945 and 7,094,809 disclose several hydroxytolan compounds and their use in inhibiting the formation of infectious herpes virus particles or for treating gonorrhea caused by *Neisseria gonorrhoeae*. WO2009/126700 discloses the use of similar compounds for skin care, such as UV radiation, and cosmetic uses. And U.S. Pat. No. 8,716,355 (WO2011/0130468) and 8,680,142 (WO2011/0160301) disclose similar hydroxytolans for use as anti-tumor agents. However, the potential utility of these, or any other hydroxytolans as autophagy-modulating compounds was unknown until the making of the present invention. U.S. Pat. Nos. 6,008,260, 6,197,834 and 6,355,692 disclose certain hydroxylated stilbenes, and specifically resveratrol. None of these references disclose the use of such modified tolan or stilbene compounds as autophagy modulating agents.

It would be advantageous if the process of autophagy could be modulated, that is stimulated or enhanced in some conditions, and slowed or suppressed in other conditions.

SUMMARY OF THE INVENTION

The present invention relates to compounds, formulations, and methods for modulating autophagy, particularly for the indication or purpose of promoting wound healing in a patient having a chronic wound or skin condition. In one aspect, the invention comprises a method of promoting wound healing comprising administering at least one first autophagy modulating (FAM) compound as described herein. In most embodiments for promotion of wound healing, the autophagy modulation is directionally upregulation of autophagy activity. In certain embodiments, the FAM is administered with an auxiliary autophagy modulator (AAM) compound. The FAM and AAM may be co-administered or administered one prior to the other. If co-administered, they may be formulated in the same dosage form or as two distinct dosages or drug products. The AAM may modulate the effect of the FAM by either stimulating or increasing its effect, or by depressing or inhibiting its effect since many are hormetic compounds.

These autophagy modulators are liquid crystalline in nature and act in specific combinations to treat a wound or skin related disease or condition. The invention further describes the use of these liquid crystals to create bioactive formulations such as hydrogels and alginates that can also serve as bioactive membranes to promote healing in a wound or skin related condition. Thus, in some aspects, the invention comprises a formulation containing a FAM and AAM. The formulation may be a hydrogel, such as an alginate. The formulation may include a cationic salt of an FAM, or a complex of an FAM and an AAM with a cation. In other formulations, the FAM and/or AAM may be formulated with a cyclodextrin.

The specific FAM may be a tolan or stilbene (including cis and trans stilbenes) and may have any of a variety of substituents as described herein. In some embodiments, the substituents are hydroxyl or alkoxyl groups that increase solubility and polarity of the molecule. Any FAM may be administered with any AAM. For example, the FAM may be a tolan and the AAM may be a vitamin, acidic sugar, amino acid, or quinolone. Likewise, the FAM may be a stilbene and the AAM may be a vitamin, acidic sugar, amino acid, or quinolone.

In some aspects, the method promotes wound healing in specific indications, such as wherein the wound or skin condition is one or more selected from: aging, autoimmune diseases with inflammation, avascular necrosis, bacterial infection, cancers, diabetic neuropathies, endometriosis, fungal infection, gout, hairloss, infectious arthritis, inflammation, inflammatory bowel, ischemia, Lyme disease, organ/tissue transplant, parasitic infection, psoriatic arthritis, psoriasis, pseudogout, rheumatoid arthritis, scleroderma, scurvy, sepsis, skin diseases, surgical scars, surgical adhesions, transfection procedures, ulcerative colitis, ulcers, viral infection, warts, surgical wounds, incisions, lacerations, cuts and scrapes donor site wounds from skin transplants, traumatic wounds, infectious wounds, ischemic wounds, burns, bullous wounds, aseptic wounds, contused wounds, incised wounds, lacerated wounds, non-penetrating wounds, open wounds, penetrating wounds, perforating wounds, puncture wounds, septic wounds, subcutaneous wounds, chronic ulcers, gastric ulcers, skin ulcers, peptic ulcer, duodenal ulcer, gastric ulcer, gouty ulcer, hypertensive ischemic ulcer, stasis ulcer, sublingual ulcer, submucous ulcer, symptomatic ulcer, trophic ulcer, tropical ulcer and venereal ulcer.

In some methods, the wound to be healed is dermatological in nature, such as cuts, abrasions, ulcers of many types and degrees, aging, skin inelasticity, and the like. In other methods, the wound may be ophthalmic or optic; in other methods, the wound may be oral in nature, such as cancer sores, herpes viral infections, tooth extraction wounds, gingivitis, or the like.

BRIEF DESCRIPTION OF THE DRAWINGS

The accompanying drawings, incorporated herein and forming a part of the specification, illustrate the present invention in its several aspects and, together with the description, serve to explain the principles of the invention. In the drawings, the thickness of the lines, layers, and regions may be exaggerated for clarity.

Figure 1:
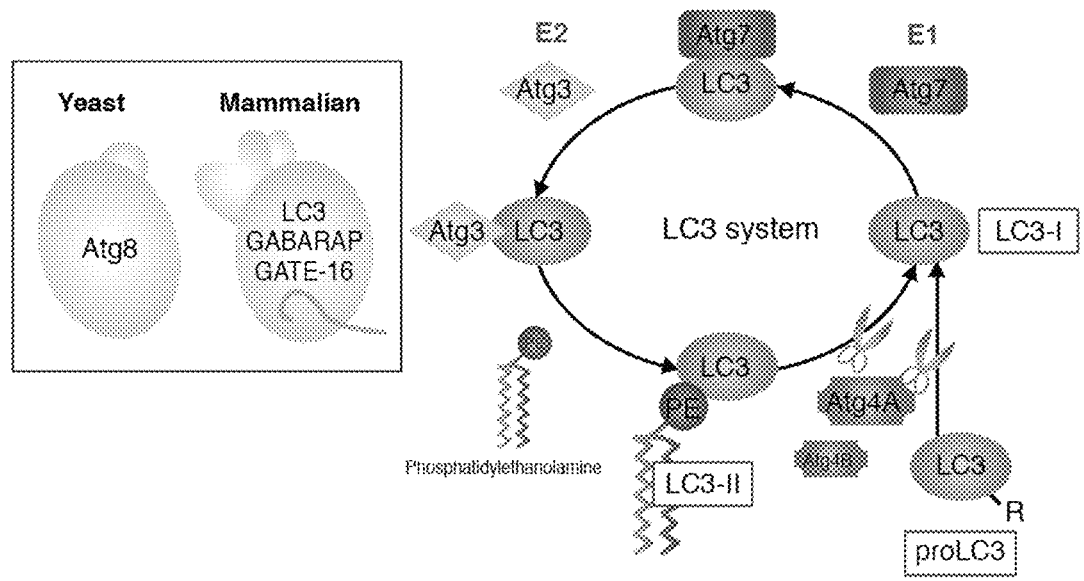
FIG. 1 is a schematic illustration showing the role of LC3 in autophagy.

The accompanying drawings, incorporated herein and forming a part of the specification, illustrate the present invention in its several aspects and, together with the description, serve to explain the principles of the invention. In the drawings, the thickness of the lines, layers, and regions may be exaggerated for clarity.

DETAILED DESCRIPTION

Numerical ranges, measurements and parameters used to characterize the invention—for example, angular degrees, quantities of ingredients, polymer molecular weights, reaction conditions (pH, temperatures, charge levels, etc.), physical dimensions and so forth—are necessarily approximations; and, while reported as precisely as possible, they inherently contain imprecision derived from their respective measurements. Consequently, all numbers expressing ranges of magnitudes as used in the specification and claims are to be understood as being modified in all instances by the term "about." All numerical ranges are understood to include all possible incremental sub-ranges within the outer boundaries of the range. Thus, a range of 30 to 90 units discloses, for example, 35 to 50 units, 45 to 85 units, and 40 to 80 units, etc. Unless otherwise defined, percentages are weight/weight (wt/wt); although formulations are generally weight/volume (w/v), in grams per 100 mL (which is equivalent to wt/wt with aqueous solutions having a density of 1.0), and area of wounds is expressed in $cm^2$ as area/area (a/a).

All patents, published patent applications, and non-patent literature references cited herein are incorporated herein by reference in their entirety.

In some aspects, the invention comprises methods of modulating autophagy comprising the administration of a first autophagy modulator (FAM) compound and optionally an auxiliary autophagy modulator (AAM) compound. The FAM and AAM compounds are described in more detail in sections below. They may be given sequentially or concomitantly. If given sequentially, the order may be FAM first, then AMM, or AMM first, then FAM. If given concomitantly, they may be given in separate, individual drug products or a single drug product as a combination of ingredients. The compounds may be administered from once daily up to about 6 times per day, depending on the formulation excipients. Administration routes include topical, transdermal, oral, nasal, ophthalmic, optic, IV, IM, subcutaneous, rectal, and vaginal.

The use of pharmaceutical excipients in the preparation of drug products is generally well understood from pharmaceutical treatises such as Remington's Pharmaceutical Sciences, 18$^{th}$ Edition (1990) and its subsequent editions, like Remingtons: The Science and Practice of Pharmacy, 22$^{nd}$ edition (2012). Topical formulations may be combined with solvents, emulsifiers, emollients, solvents, etc. into solutions, suspensions, creams, ointments and hydrogels, among others.

In certain embodiments, the invention involves a formulation containing a FAM compound and an AAM compound. The relative amounts of FAM to AAM in a formulation expressed as a molar ratio may range from about 500:1 to about 1:500 (FAM:AAM), or, in certain embodiments, from about 200:1 to 1:200. In liquid formulations, the FAM may comprise from about 0.01% to about 40% (w/v) of the formulation and the AMM may comprise from about 0.01% to about 99.9% (w/v) of the formulation. In certain embodiments, the FAM may comprise from about from about 0.1% to about 40% (w/v) of the formulation and the AMM may comprise from about 0.1% to about 60% (w/v) of the formulation. Optimally the formulation concentration of an FAM is between 0.5-15% (w/v).

Chemical and Biological Definitions

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are described herein. All references cited herein, including books, journal articles, published U.S. or foreign patent applications, issued U.S. or foreign patents, and any other references, are each incorporated by reference in their entireties, including all data, tables, figures, and text presented in the cited references.

The following terms used throughout this application have the meanings ascribed below.

A "first autophagy modulator" or "FAM compound" or "FAM" means a compound of formula I:

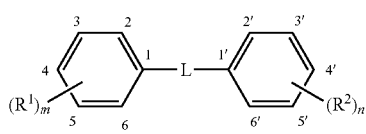

(I)

wherein L is a linker selected from: —C≡C— and —CR$_a$=CR$_b$—;

R$_a$ and R$_b$ are independently H or phenyl optionally substituted with —(R$^3$)$_p$ or —(R$^4$)$_q$;

R$^1$ to R$^4$ are independently substituents at any available position of the phenyl rings;

m, n, p and q are, independently, 0, 1, 2, or 3 representing the number of substituents on the rings, respectively, and at least one of m or n must be ≥1;

wherein each R$^1$, R$^2$, R$^3$, and R$^4$ is independently selected from:

R$^5$, wherein R$^5$ is selected from (C$_1$-C$_6$)alkyl, (C$_2$-C$_6$) alkenyl, or (C$_2$-C$_6$)alkynyl; optionally substituted with 1 to 3 substituents selected from —OH, —SH, -halo, —NH$_2$, or NO$_2$;

YR$^6$, wherein Y is O, S, or NH; and R$^6$ is selected from H or R$^5$;

ZR$^5$, wherein Z is —N(C=O)— or —O(C=O)—;

halo;

NO$_2$;

SO$_3$Na;

azide; and glycosides and salts thereof;

with the proviso that the FAM is not resveratrol or 4,4'-(ethyne-1,2-diyl)diphenol (TOLCINE).

An "auxiliary autophagy modulator" or "AAM compound" or "AAM" means a compound as described herein that also has an autophagy modulating effect. The effect may be stimulatory or inhibitory depending on the compound. While not intending to be bound by any particular theory, AAM compounds may have inhibitory action by competing for a rate limiting step, such as cellular uptake mechanisms. More specific AAM compounds are described in a subsequent section.

Autophagy modulation refers to either up-regulation or down-regulation of the process of autophagy in the cell. Depending on the particular disease state or condition, it may be desirable to achieve one or the other direction of regulation of autophagy, as is described later. And, referring to the discussion of hormesis, the dose of any particular FAM or AAM compound or combination or complex may achieve up-regulation or down-regulation or both.

As used herein, the term "—(C$_1$-C$_6$)alkyl" refers to straight-chain and branched non-cyclic saturated hydrocarbons having from 1 to 6 carbon atoms. Representative straight chain —(C$_1$-C$_6$)alkyl groups include methyl, -ethyl, -n-propyl, -n-butyl, -n-pentyl, and -n-hexyl. Representative branched-chain —(C$_1$-C$_6$)alkyl groups include isopropyl, sec-butyl, isobutyl, tert-butyl, isopentyl, neopentyl, 1-methylbutyl, 2-methylbutyl, 3-methylbutyl, 1,1-dimethylpropyl, and 1,2-dimethylpropyl, methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, and the like. More generally, the subscript refers to the number of carbon atoms in the chain. Thus, the term "—(C$_1$-C$_4$)alkyl" refers to straight-chain and branched non-cyclic saturated hydrocarbons having from 1 to 4 carbon atoms.

As used herein, the term "—(C$_2$-C$_6$)alkenyl" refers to straight chain and branched non-cyclic hydrocarbons having from 2 to 6 carbon atoms and including at least one carbon-carbon double bond. Representative straight chain and branched —(C$_2$-C$_6$)alkenyl groups include -vinyl, allyl, -1-butenyl, -2-butenyl, -isobutylenyl, -1-pentenyl, -2-pentenyl, -3-methyl-1-butenyl, -2-methyl-2-butenyl, and the like.

As used herein, the term "—(C$_2$-C$_6$)alkynyl" refers to straight chain and branched non-cyclic hydrocarbons having from 2 to 6 carbon atoms and including at least one carbon-carbon triple bond. Representative straight chain and branched —(C$_2$-C$_6$)alkynyl groups include -acetylenyl, -propynyl, -1 butynyl, -2-butynyl, -1-pentynyl, -2-pentynyl, -3-methyl-1-butynyl, -4-pentynyl, and the like.

As used herein, "—($C_1$-$C_{10}$)alkoxy" means a straight chain or branched non-cyclic hydrocarbon having one or more ether groups and from 1 to 10 carbon atoms. Representative straight chain and branched ($C_1$-$C_{10}$)alkoxys include -methoxy, -ethoxy, -propoxy, -butyloxy, -pentyloxy, -hexyloxy, -heptyloxy, -methoxymethyl, -2-methoxyethyl, -5-methoxypentyl, -3-ethoxybutyl and the like.

As used herein, "—($C_1$-$C_6$)alkoxy" means a straight chain or branched non-cyclic hydrocarbon having one or more ether groups and from 1 to 6 carbon atoms. Representative straight chain and branched ($C_1$-$C_5$)alkoxys include -methoxy, -ethoxy, -propoxy, -butyloxy, -pentyloxy, -hexyloxy, -methoxymethyl, -2-methoxyethyl, -5-methoxypentyl, -3-ethoxybutyl and the like.

As used herein, the term "—($C_3$-$C_{12}$)cycloalkyl" refers to cyclic saturated hydrocarbon having from 3 to 12 carbon atoms. Representative ($C_3$-$C_{12}$)cycloalkyls include cyclopropyl, cyclobutyl, cyclopentyl, cyclohexyl, cycloheptyl, cyclooctyl, and cyclononyl, cyclodecyl, cycloundecyl, cyclododecyl, and the like.

As used herein, the term "—($C_4$-$C_{12}$)cycloalkenyl" refers to a cyclic hydrocarbon having from 4 to 12 carbon atoms, and including at least one carbon-carbon double bond. Representative —($C_3$-$C_{12}$)cycloalkenyls include -cyclobutenyl, -cyclopentenyl, -cyclopentadienyl, -cyclohexenyl, -cyclohexadienyl, -cycloheptenyl, -cycloheptadienyl, -cycloheptatrienyl, -cyclooctenyl, -cyclooctadienyl, -cyclooctatrienyl, -cyclooctatetraenyl, -cyclononenyl, -cyclononadienyl, -cyclodecenyl, -cyclodecadienyl, -norbornenyl, and the like.

As used herein a "-(7- to 12-membered)bicyclic aryl" means an bicyclic aromatic carbocyclic ring containing 7 to 12 carbon atoms. Representative -(7- to 12-membered) bicyclic aryl groups include -indenyl, -naphthyl, and the like.

As used herein a "hydroxy($C_1$-$C_6$)alkyl" means any of the above-mentioned $C_{1-6}$ alkyl groups substituted by one or more hydroxy groups. Representative hydroxy($C_1$-$C_6$)alkyl groups include hydroxymethyl, hydroxyethyl, hydroxypropyl and hydroxybutyl groups, and especially hydroxymethyl, 1-hydroxyethyl, 2-hydroxyethyl, 1,2-dihydroxyethyl, 2-hydroxypropyl, 3-hydroxypropyl, 3-hydroxybutyl, 4-hydroxybutyl, 2-hydroxy-1-methylpropyl, and 1,3-dihydroxyprop-2-yl.

Any of the groups defined above may be optionally substituted. As used herein, the term "optionally substituted" refers to a group that is either unsubstituted or substituted. Optional substituents, when present and not otherwise indicated, include 1, 2, or 3 groups each independently selected from the group consisting of —($C_1$-$C_6$)alkyl, OH, halo, —C(halo)$_3$, —CH(halo)$_2$, —CH$_2$(halo), NH$_2$, —NH($C_1$-$C_6$) alkyl, CN, SH, phenyl, benzyl, (=O), halo($C_1$-$C_6$)alkyl-, hydroxy($C_1$-$C_6$)alkyl-. Thus, certain substituted embodiments include those named below.

As used herein a "dihydroxy($C_1$-$C_6$)alkyl" means any of the above-mentioned $C_{1-6}$ alkyl groups substituted by two hydroxy groups. Representative dihydroxy($C_1$-$C_6$)alkyl groups include dihydroxyethyl, dihydroxypropyl and dihydroxybutyl groups, and especially 1,2-dihydroxyethyl, 1,3-dihydroxypropyl, 2,3-dihydroxypropyl, 1,3-dihydroxybutyl, 1,4-dihydroxybutyl, and 1,3-dihydroxyprop-2-yl.

As used herein, the terms "halo" and "halogen" refer to fluoro, chloro, bromo or iodo.

As used herein, "—CH$_2$(halo)" means a methyl group where one of the hydrogens of the methyl group has been replaced with a halogen. Representative —CH$_2$(halo) groups include —CH$_2$F, —CH$_2$Cl, —CH$_2$Br, and —CH$_2$I.

As used herein, "—CH(halo)$_2$" means a methyl group where two of the hydrogens of the methyl group have been replaced with a halogen. Representative —CH(halo)$_2$ groups include —CHF$_2$, —CHCl$_2$, —CHBr$_2$, —CHBrCl, —CHClI, and —CHI$_2$.

As used herein, "—C(halo)$_3$" means a methyl group where each of the hydrogens of the methyl group has been replaced with a halogen. Representative —C(halo)$_3$ groups include —CF$_3$, —CCl$_3$, —CBr$_3$, and —CI$_3$.

As used herein, "(halo)$_p$($C_1$-$C_6$)alkyl-" means a ($C_1$-$C_6$) alkyl chain substituted with halo in p locations, where p is 1, 2 or 3. The halo substituents may be substituted on the same or a different carbon in the ($C_1$-$C_6$)alkyl. Representative "(halo)$_p$($C_1$-$C_6$)alkyl-" groups include, for example —CH$_2$CHF$_2$, —CH$_2$CH$_2$CH$_2$Cl, —CHBr$_2$, —CHBrCl, —CHClI, —CH$_2$CHI$_2$, —CH$_2$CH$_2$CHClCH$_2$Br, and the like.

As used herein, "azide" means a substituent of the formula —N=N=N.

As used herein, "glycoside" means a 5- or 6-membered cyclic sugar connected to the compound of Formula I. The bond is generally a glycosidic bond from an anomeric carbon of the sugar, and may be made via: (1) an oxygen atom, thus forming an "O-glycoside", (2) a nitrogen atom, thus forming an "N-glycoside" or (3) a sulfur atom, thus forming an "S-glycoside." Glycosides may be mono- or di-saccharides, having one or two ring structures. Representative glycosides formed from 6 membered sugars glucosides, galactosides, mannosides, and altrosides; and glycosides formed from the 5 membered sugars, include ribosides, arabinosides, xylosides and lyxosidees. The sugars may contain optional substituents, but many embodiments contain only the native —H and —OH substituents that define the respective sugars.

Overlap exists in the literature among use of the terms "wound," "ulcer," and "sore" and, furthermore, the terms are often used at random. Therefore, in the present context the term "wounds" encompasses the term "ulcer", "lesion", "sore" and "infarction", and the terms are used interchangeably unless otherwise indicated. Wounds have been classified by many criteria, including size or area (large or small), depth or layer involvement, causation, difficulty in healing, etc. Some classify wounds by i) small tissue loss due to surgical incisions, minor abrasions and minor bites, or as ii) significant tissue loss, such as in ischemic ulcers, pressure sores, fistulae, lacerations, severe bites, thermal burns and donor site wounds (in soft and hard tissues) and infarctions. All types and classification of wounds are encompassed by the invention.

The term "skin" is used in a very broad sense embracing the epidermal layer of the integument and, in those cases where the skin surface is more or less injured, also the dermal layer beneath. Apart from the stratum corneum, the epidermal layer of the skin is the outer (epithelial) layer and the deeper connective tissue layer of the skin is called the "dermis," which contains the nerves and terminal organs of sensation.

A method that "promotes the healing of a wound" results in the wound healing more quickly as a result of the treatment than a similar wound heals in the absence of the treatment. "Promotion of wound healing" can also mean that the method regulates the proliferation and/or growth of, inter alia, keratinocytes, or that the wound heals with less scarring, less wound contraction, less collagen deposition and more superficial surface area. In certain instances, "promotion of wound healing" can also mean that certain methods of wound healing have improved success rates, (e.g., the take rates of skin grafts) when used together with the method of the present invention.

The phenomenon of hormesis is commonly associated with compounds that induce biologically opposite effects in a dose dependent fashion, and is well described in the literature, for example: Calabrese E J, Bachmann K A, Bailer A J, Bolger P M, Borak J, et al. (2007), *Biological stress response terminology: Integrating the concepts of adaptive response and preconditioning stress within a hormetic dose-response framework*. Toxicol Appl Pharmacol. 222:122-128; Penniston K L, Tanumihardjo S A. *The acute and chronic toxic effects of vitamin A*. Am J Clin Nutr. 2006; 83:191-201; and Cook R, Calabrese E J. *The importance of hormesis to public health*. Cien saude Colet. 2007; 12:955-963. Commonly there is a stimulatory or beneficial effect at low doses and an inhibitory or toxic effect at high doses. Hormesis has also been characterized as autoprotection, adaptive response, and preconditioning, among others; and by the shape of its dose response curve including: e.g. β-curve, biphasic, bell-shaped, U-shaped or inverted-U shaped, bimodal, functional antagonism, and dual response, among others. Known hormetic substances (or "hormetins") include: vitamin A, ferulic acid, chalcone, rapamycin, epigallocatechin-3-gallate and many others.

Hormesis can also represent adaptive responses where a moderate stress is applied in order to provide the organism with adaptive resistance when faced with a severe stressor. Environmental stresses such as oxidative metabolic and thermal stress serve as hormetins used to induce a specific response or adaptive change (Mattson M P. *Hormesis defined*, Ageing Res Rev. 2008; 7:1-7). Hormetins have been shown to activate various stress and detoxification pathways including; heat shock proteins, antioxidant, protein chaperones, metabolism, calcium homeostasis and growth factors (Mattson M P, Cheng A. *Neurohormetic phytochemicals: Low-dose toxins that induce adaptive neuronal stress responses*. Trends Neurosc. 2006; 29:632-639; and Mattson, 2008, noted above). These dose response effects have been analyzed for a range of natural signaling molecules including nitric oxide, adenosine, opioids, adrenergic agents, prostaglandins, estrogens, androgens, 5-hydroxytryptamine and dopamine (Calabrese E J, Bachmann K A, Bailer A J, Bolger P M, Borak J, et al. (2007), *Biological stress response terminology: Integrating the concepts of adaptive response and preconditioning stress within a hormetic dose-response framework*. Toxicol Appl Pharmacol. 222:122-128 and Hayes D P. *Nutritional hormesis*. Eur J Clin Nutr. 2007; 61:147-159) Many of these hormetics are concentrated by bacteria, fungi, viruses and plants to protect themselves from predatory species. However, when many of these substances are utilized in lower concentrations they can have beneficial effects.

A hydrogel is a dilute cross-linked aqueous system comprising water and a gelling agent such as a polymeric plastic or polysaccharide which can absorb and retain significant amounts of water to form three-dimensional network structures. The hydrogel structure is created by the interaction of water with hydrophilic groups or domains present in the polymeric network upon hydration. Hydrogels are categorized principally as weak or strong depending on their flow behavior in steady-state.

Gelation occurs when the polymer concentration increases, and disperses polymers begin to branch and form crosslinks. Once a critical concentration is reached the sol becomes a gel and the sol-gel transition occurs. Gels may be considered chemically linked or physically linked. Physical gels can be subcategorized as strong or weak, depending on the nature of the bonds, with strong physical approaching chemical gels in linkage permanence. Strong physical bonds include: lamellar microcrystals, glassy nodules or double and triple helices; whereas weak physical gels include: hydrogen bonds, block copolymers, micelles, and ionic associations.

Hydrogels, due to their significant water content possess a degree of flexibility similar to natural tissue, and may exhibit viscoelastic or pure elastic behavior, and stickiness. Properties of a hydrogel may be modified by controlling the polarity, surface properties, mechanical properties, and swelling behavior. Gels may exhibit significant volume changes in response to small changes in pH, ionic strength, temperature, electric field, and light. Biodegradable hydrogels, containing labile bonds, are advantageous in applications such as tissue engineering, wound healing and drug delivery. These labile bonds can be present either in the polymer backbone or in the cross-links used to prepare the hydrogel. The labile bonds can be broken under physiological conditions either enzymatically or chemically, in most of the cases by hydrolysis (Bajpai, A. K., Shukla, S. K., Bhanu, S. & Kankane, S. (2008). Responsive polymers in controlled drug delivery. Progress in Polymer Science. 33: 1088-1118).

Ionic polymers having negatively charged groups at physiological pH can be cross-linked by the addition of multivalent cations; and even monovalent cations (e.g. $K^+$, $Na^+$, etc.) may shield or screen the repulsion of negatively charged groups (e.g. $SO^-_3$) to form stable gels. Examples include: $Na^+$ alginate$^-$; chitosan-polylysine; chitosan-glycerol phosphate salt (Syed K. H. Gulrez$^1$ and Saphwan Al-Assaf. Progress in molecular and environmental bioengineering from analysis and modeling to technology applications Chapter 5: Hydrogels: Methods of preparation, characterization and applications. Publisher InTech. Aug. 1, 2011(34)) and chitosan-dextran hydrogels (Hennink, W. E. & Nostrum, C. F. (2002). Novel crosslinking methods to design hydrogels. Advanced drug delivery reviews. 54: 13).

Alginate is a naturally occurring anionic polysaccharide typically obtained from brown seaweed, and has been extensively investigated and used for many biomedical applications, due to its biocompatibility, low toxicity, relatively low cost, and ability to form hydrogels by addition of divalent cations such as $Ca^{2+}$. Alginate hydrogels have been used in a variety of applications including; wound healing and drug delivery. Alginate wound dressings maintain a moist wound environment, minimize bacterial infection at the wound site, and facilitate wound healing. Drug molecules can be released from alginate gels in a controlled manner, depending on the cross-linker and cross-linking methods employed. In addition, alginate gels can be orally administrated or injected, making them extensively useful in the pharmaceutical arena.

Alginates are polysaccharides constituted by variable amounts of β-D-mannuronic acid and its C5-epimer α-L-guluronic acid linked by 1-4 glycosidic bonds. The capability of alginate to confer viscosity in sol-gels is dependent on its molecular mass (MM). The molecular mass (MM) of algal alginates has been found to range from 48 to 186 kDa (38); whereas some alginates isolated from *A. vinelandii* present MM in the range of 80 to 4,000 kDa (Galindo, E.; Peria, C.; Núñez, C.; Segura, D. & Espin, G. (2007). Molecular and bioengineering strategies to improve alginate and polyhydroxyalkanoate production by *Azotobacter vinelandii*. Microbial Cell Factories, 6, 1-1). The saccharide monomers are distributed in blocks of continuous mannuronate residues (M), guluronate residues (G) or alternating residues (MG), depending on the source species Smidsrod, O. & Draget, K. (1996). Chemistry and physical properties of alginates. Carbohydrates European, 14, 6-12). The G-blocks of alginates participate in intermolecular cross-linking with divalent cations (e.g., $Ca^{2+}$) to form hydrogels.

The composition (i.e., M/G ratio), sequence, G-block length, and molecular weight are critical factors which alter the physical properties (e.g. increasing G-block length increases ionic binding and the mechanical rigidity of the gel) of alginate and alginate hydrogels. These same properties control the stability of the gels along with the release rate of alginates containing drugs. Alginates with a low M/G ratio form strong and brittle gels, while alginates with a high M/G ratio form weaker and softer, but more elastic gels. Finally, bacterial alginates are acetylated to a variable extent at positions O-2 and/or O-3 of the mannuronate residues (Skjak-Braek, G.; Grasdalen, H. & Larsen, B. (1986). Monomer sequence and acetylation pattern in some bacterial alginates. Carbohydrates Research, 154, 239-250). The variability in molecular mass, monomer block structure and acetylation all influence the physicochemical and rheological characteristics of the gel polymer.

The majority of alginates use the divalent cation calcium or monovalent ions such as $Na^+$ or $K^+$ while other ions such as $Mg^{2+}$ have been proposed but for the gelation process to occur the concentration of magnesium ions required is 5-10 times higher than that of calcium (Topuz, F., Henke, A., Richtering, W. & Groll, J. (2012). Magnesium ions and alginate do form hydrogels: a rheological study. Soft Matter. 8:4877-4881). Alginates may have decreased water solubility such as alginic acid or calcium alginate where the ion is shielded from ionization resulting in insoluble alginates. Water soluble alginates can be made simply by creating salts using monovalent anions such as $Na^+$ or $K^+$ or a non polar group such as $NH_4$ which is generally water soluble.

First Autophagy Modulators (FAMs)

As noted, the first autophagy modulators are compounds of Formula I, which comprises two phenyl rings joined by a linker, L, and having at least one $R^1$ or $R^2$ attached to a phenyl ring. In some embodiments, L is —C≡C— and these FAM compounds are known as "tolans," which are generally linear from phenyl ring to phenyl ring. In other embodiments, L is —CH=CH— and these FAM compounds are known as "stilbenes" which are isomeric in cis and trans forms about the double bond. In some embodiments the FAM compound is a trans stilbene. In still other embodiments, L is —$CR_a$=$CR_b$— where $R_a$ and/or $R_b$ may be a phenyl ring or H. These are also stilbenes, in this case "phenyl stilbene derivatives" and they may also be trans stilbenes or cis stilbenes.

There are two "primary" phenyl rings shown in the structure and containing substituents $R^1$ and $R^2$, of which at least one must be present (i.e. at least one of m or n is ≥1). Optionally, there are also up to two "secondary" phenyl rings within the options for $R_a$ and $R_b$. On each phenyl ring (up to four possible, two primary and two secondary) there may be from zero to five of each substituent $R^{1-4}$. In certain embodiments, there are from one to three $R^1$, and/or from one to three $R^2$ substituents on the primary phenyl rings. In some embodiments, the position of $R^1$ and/or $R^2$ on the primary phenyl rings is mostly at the para and meta positions, namely the 3, 4 or 5 position on one phenyl ring and the 3', 4' and 5' positions on the other phenyl ring, although it is also possible to have substituents in the ortho position (2, 2', 6 and 6'). There may be one, two or three $R^1$ substituents on the first phenyl ring, and correspondingly, from zero to three $R^2$ substituents on the second phenyl ring. Conversely, there may be one, two or three $R^2$ substituents on the second phenyl ring, and correspondingly, from zero to three $R^1$ substituents on the first phenyl ring. Additionally, in some embodiments, the secondary phenyl rings may contain one to three substituents $R^3$ and $R^4$. All permutations within these are possible, for example: one $R^1$ and one $R^2$; two $R^1$ and two $R^2$; three $R^1$ and three $R^2$; one $R^1$ and two $R^2$; one $R^1$ and three $R^2$; two $R^1$ and one $R^2$; two $R^1$ and two $R^2$; two $R^1$ and three $R^2$; three $R^1$ and one $R^2$; or three $R^1$ and two $R^2$. Likewise with $R^3$ and $R^4$. Each $R^{1-4}$ is independently selected and if two or more are present they may be the same or different. Examples of some specific first autophagy modulators are given in Table A, the tolans being analogues of the stilbenes so detailed structures are not necessary for each individual compound.

TABLE A

Certain Representative FAM compounds
The nature and position(s) of $R^1$ and $R^2$ substituents

| Stilbenes | Tolans |
|---|---|
| 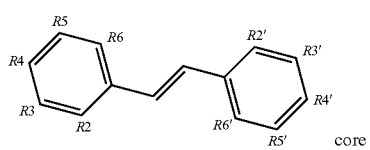 core | 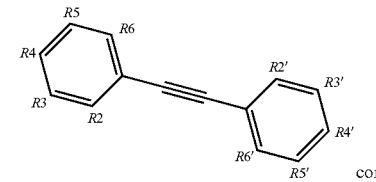 core |
| Hydroxy 3,5-dihydroxy-trans-stilbene (aka, Pinosylvin); 3,4-dihydroxy-trans-stilbene, 3,4,5-trihydroxy-trans-stilbene, 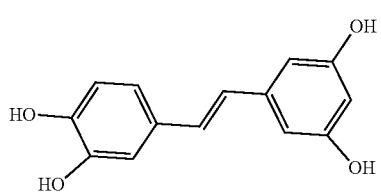 [SMILES: Oc1cc(O)cc(/C=C/c2ccc(O)c(O)c2)c1] 3,3',4,5'-tetrahydroxy-trans-stilbene (aka piceatannol); and 3,3',4,4'-tetrahydroxy-trans-stilbene 3,4,4'-trihydroxy-trans-stilbene; | 3,5-dihydroxytolan, 3,4-dihydroxytolan, 3,4,5-trihydroxytolan, 3,3',4,5'-tetrahydroxytolan; and 3,3',4,4'-tetrahydroxytolan 3,5,4'-trihydroxytolan 3,4,4'-trihydroxytolan; 3,3',4'-trihydroxytolan; 2,4,4'-trihydroxytolan; 2,4,2',4'-tetrahydroxytolan |

TABLE A-continued

Certain Representative FAM compounds
The nature and position(s) of $R^1$ and $R^2$ substituents Stilbenes 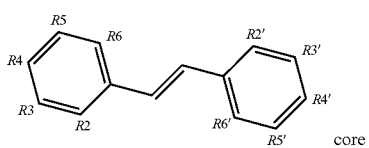   Tolans 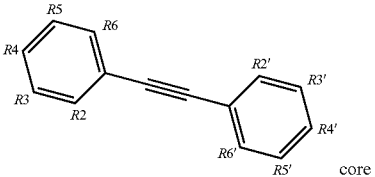

core

| | Stilbenes | Tolans |
|---|---|---|
| Alkyl and mixed | 3,3',4'-trihydroxy-trans-stilbene; 4,4'-dihydroxy-trans-stilbene; 2,4,4'-trihydroxy-trans-stilbene; 2,4,2',4'-tetrahydroxy-trans-stilbene 3,5-dihydroxy-4-ethylstilbene, 3,5-dihydroxy-4'-ethylstilbene; 3,5-dihydroxy-4-isopropyl-trans-stilbene; 3,5-dihydroxy-4-isopropyl-trans-4'-hydroxystilbene; 3,5-dihydroxy-4-isopropyl-trans-3',4'-dihydroxystilbene; 3,5-dihydroxy-4-isopropyl-trans-3',5'-dihydroxystilbene; 3,5-dihydroxy-4-isopropyl-trans-3',4',5'-trihydroxystilbene 3,4-dihydroxy-4'-isopropyl-trans-stilbene; 3,5-dihydroxy-4'-isopropyl-trans-stilbene; 3,4,5-trihydroxy-4'-isopropyl-trans-stilbene; 4-hydroxy-4'-isopropyl-trans-stilbene; 4'-hydroxy-3,4-dimethyl-trans-stilbene, 4'-hydroxy-3,4,5-trimethyl-trans-stilbene, 4'-hydroxy-4,5-dimethyl-trans-stilbene | 3,5-dihydroxy-4-ethyltolan, 3,5-dihydroxy-4'-ethyltolan 3,5-dihydroxy-4-isopropyltolan; and 3,5-dihydroxy-4-isopropyl-trans-4'hydroxytolan; 3,5-dihydroxy-4-isopropyl-trans-3',4'-dihydroxytolan; 3,5-dihydroxy-4-isopropyl-trans-3',5'-dihydroxytolan; 3,5-dihydroxy-4-isopropyl-trans-3',4',5'-trihydroxytolan 3,4-dihydroxy-4'-isopropyltolan; 3,5-dihydroxy-4'-isopropyltolan; 3,4,5-trihydroxy-4'-isopropyltolan; 4-hydroxy-4'-isopropyltolan 4'-hydroxy-3,4-dimethyltolan, 4'-hydroxy-3,4,5-trimethyltolan, 4'-hydroxy-4,5-dimethyltolan. |
| Glycosides and mixed | 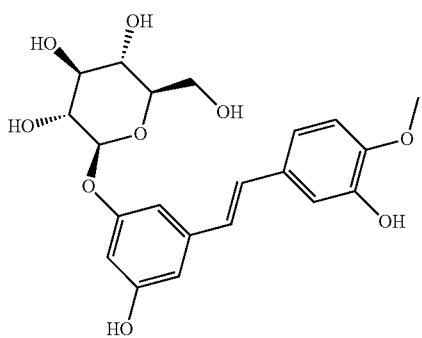 [SMILES: COc1ccc(/C=C/c2cc(O)cc(O[C@@H]3O[C@H](CO)[C@@H](O)[C@H](O)[C@H]3O)c2)cc1O]<br>E.g.<br>3,5'-dihydroxy-4'-methoxystilbene-5-O-β-D-glucoside<br>3',4'-dihydroxy-3-methoxystilbene 5-O-β-D-glucoside;<br>3,4'-dihydroxystilbene 5-O-β-D-glucoside;<br>2,3-dihydroxy-4'-methoxystilbene 5-O-β-D-glucoside;<br>2,3,3'-trihydroxy-4'''-methoxystilbene 5-O-β-D-glucoside | E.g.<br>3,5'-dihydroxy-4'-methoxytolan 5-O-β-D-glucoside;<br>3',4'-dihydroxy-3-methoxytolan-5-O-β-D-glucoside;<br>3,4'-dihydroxytolan 5-O-β-D-glucoside;<br>2,3-dihydroxy-4'-methoxytolan 5-O-β-D-glucoside;<br>2,3,3'-trihydroxy-4'-methoxytolan 5-O-β-D-glucoside; |

TABLE A-continued

Certain Representative FAM compounds
The nature and position(s) of R¹ and R² substituents

| | Stilbenes | Tolans |
|---|---|---|
| Halo and mixed | 3,5-dihydroxy-4'-chlorostilbene, 3,4-dihydroxy-4'-chlorostilbene, or 4,5-dihydroxy-4'-chlorostilbene, 3,4,5-dihydroxy-4'-chlorostilbene, and 2,3,4,5,6-penthydroxy-4'-chlorostilbene 3,4-dihydroxy-4'-fluorostilbene, or 4,5-dihydroxy-4'-fluorostilbene, 3,4,5-trihydroxy-4'-fluorostilbene, 3,5-dihydroxy-4'-fluorostilbene, 3,4-dihydroxy-4' (trifluoro)methylstilbene | 3,5-dihydroxy-4'-chlorotolan, 3,4-dihydroxy-4'-chlorotolan, or 4,5-dihydroxy-4'-chlorotolan, 3,4,5-dihydroxy-4'-chlorotolan 3,4-dihydroxy-4'-fluorotolan or 4,5-dihydroxy-4'-fluorotolan, 3,4,5-trihydroxy-4'-fluorotolan, 3,5-dihydroxy-4'-fluorotolan 3,4-dihydroxy-4' (trifluoro)methyltolan |
| Thiol and mixed | 3,5-dihydroxy-4'-thiolstilbene, 3,4-dihydroxy-4'-thiolstilbene, or 4,5-dihydroxy-4'-thiolstilbene, 3,4,5-dihydroxy-4'-thiolstilbene, 3,4'-dithiol-trans-stilbene, 4,4'-dithiol-trans-stilbene, | 3,5-dihydroxy-4'-thioltolan, 3,4-dihydroxy-4'-thioltolan, or 4,5-dihydroxy-4'-thioltolan, 3,4,5-dihydroxy-4'-thioltolan, 3,4'-dithiol-tolan, 4,4'-dithiol-tolan, |
| Alkoxy (O-alkyl) and thioether (S-alkyl) and mixed | 3,5,4'-trimethoxy-trans-stilbene, 3,4,4'-trimethoxy-trans-stilbene, or 4,5,4'-trimethoxy-trans-stilbene, 3,4,5,4'-tetramethoxy-trans-stilbene, 4'-hydroxy-3,5-dimethoxy-trans-stilbene, 4'-hydroxy-3,4-dimethox-trans-stilbene, or 4'-hydroxy-4,5-dimethox-trans-stilbene, 4'-hydroxy-3,4,5-trimethox-trans-stilbene, 3,5-dihydroxy-4'-methoxy-trans-stilbene, 4,4'-dimethoxy-trans-stilbene, 3,5-dimethoxy-4'-thiomethyl-trans-stilbene 3,5,3'-trihydroxy-4'-methoxy-trans-stilbene | 3,5,4'-trimethoxytolan, 3,4,4'-trimethoxytolan, or 4,5,4'-trimethoxytolan, 3,4,5,4'-tetramethoxytolan, 4'-hydroxy-3,5-dimethoxytolan, 4'-hydroxy-3,4-dimethoxytolan, or 4'-hydroxy-4,5-dimethoxytolan, 4'-hydroxy-3,4,5-trimethoxytolan, 3,5-dihydroxy-4'-methoxytolan, 4,4'-dimethoxytolan, 3,5-dimethoxymethoxy-4'-thiomethyltolan 3,5,3'-trihydroxy-4'-methoxytolan, 4,4'-dihydroxy-3-methoxytolan 3,4-dihydroxy-4'-methoxytolan 3,4-dimethoxytolan, 3,4'-dimethoxytolan, |

TABLE A-continued

Certain Representative FAM compounds
The nature and position(s) of $R^1$ and $R^2$ substituents

| | Stilbenes | Tolans |
|---|---|---|
| | 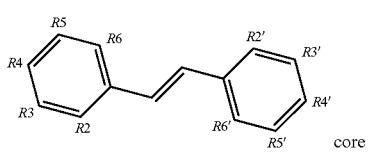 core | 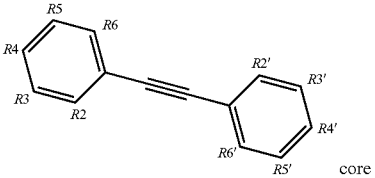 core |
| Acyl and mixed | 4,4'-dihydroxy-3-methoxy-trans-stilbene<br>3,4-dihydroxy-4'-methoxy-trans-stilbene<br>3,4-dimethoxy-trans-stilbene,<br>3,4'-dimethoxy-trans-stilbene,<br>4'hydroxy-5-acetoxy-trans-stilbene,<br>3,4-dihydroxy-5-acetoxy-trans-stilbene,<br>3,5-dihydroxy-4'-acetoxy-trans-stilbene,<br>3,4'-dihydroxy-4-acetoxy-trans-stilbene,<br>4,4'-dihydroxy-3-acetoxy-trans-stilbene,<br>3,4-dihydroxy-4'-acetoxy-trans-stilbene<br>3,4,3'-trihydroxy-4'-acetoxy-trans-stilbene,<br>3,4,4'-trihydroxy-3'-acetoxy-trans-stilbene,<br>3,5,4'-trihydroxy-3'-acetoxy-trans-stilbene,<br>3,5,3'-trihydroxy-4'-acetoxy-trans-stilbene, | 4'hydroxy-5-acetoxy-tolan,<br>3,4'-dihydroxy-5-acetoxy-tolan,<br>3,5-dihydroxy-4'-acetoxy-tolan,<br>3,4'-dihydroxy-4-acetoxytolan,<br>4,4'-dihydroxy-3-acetoxytolan,<br>3,4-dihydroxy-4'-acetoxytolan<br>3,4,3'-trihydroxy-4'-acetoxytolan,<br>3,4,4'-trihydroxy-3'acetoxytolan,<br>3,5,4'-trihydroxy-3'-acetoxytolan,<br>3,5,3'-trihydroxy-4'-acetoxytolan |
| Amide and mixed | 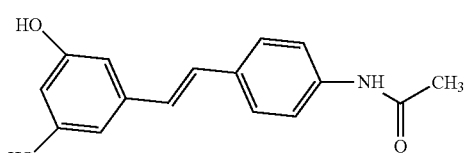<br>3,5-dihydroxy-4'-acetamide-trans-stilbene,<br>4,5-dihydyroxy-4'-acetamide-trans-stilbene, or 3,4-dihydyroxy-4'-acetamide-trans-stilbene,<br>3,4,5-trihydroxy-4'-acetamide-trans-stilbene,<br>3,4,3'-trihydyroxy-4'-acetamide-trans-stilbene,<br>3,4,5'-trihydyroxy-4'-acetamide-trans-stilbene,<br>4'hydroxy-5-acetamide-trans-stilbene,<br>3,4'-dihydroxy-5-acetamide-trans-stilbene,<br>4,4'-dihydroxy-3-acetamide-trans-stilbene,<br>3,4-dihydroxy-4'-acetamide-trans-stilbene,<br>3,4'-dihydroxy-4-acetamide-trans-stilbene,<br>4,4'-dihydroxy-3-acetamide-trans-stilbene,<br>3,4-dihydroxy-4'-acetamide-trans-stilbene<br>3,4,4'-trihydroxy-3'-acetamide-trans-stilbene,<br>3,5,4'-trihydroxy-4-acetamide-trans-stilbene,<br>3,4,3'-trihydroxy-4'-acetamide-trans-stilbene, | 3,5-dihydroxy-4'-acetamidetolan,<br>4,5-dihydyroxy-4'-acetamidetolan, or 3,4-dihydyroxy-4'-acetamidetolan,<br>3,4,5-trihydyroxy-4'-acetamidetolan,<br>3,4,3'-trihydyroxy-4'-acetamidetolan,<br>3,4,5'-trihydyroxy-4'-acetamidetolan,<br>4'-hydroxy-5-acetamidetolan,<br>3,4'-dihydroxy-5-acetamidetolan,<br>4,4'-dihydroxy-3-acetamidetolan,<br>3,4-dihydroxy-4'-acetamidetolan,<br>3,4'-dihydroxy-4-acetamidetolan,<br>4,4'-dihydroxy-3-acetamidetolan,<br>3,4-dihydroxy-4'-acetamidetolan,<br>3,4,4'-trihydroxy-3'-acetamidetolan,<br>3,5,4'-trihydroxy-4-acetamidetolan,<br>3,4,3'-trihydroxy-4'-acetamidetolan,<br>3,4,4'-trihydroxy-3'acetamidetolan,<br>3,3'-dihydroxy-4'-acetamidetolan, |

TABLE A-continued

Certain Representative FAM compounds
The nature and position(s) of $R^1$ and $R^2$ substituents Stilbenes

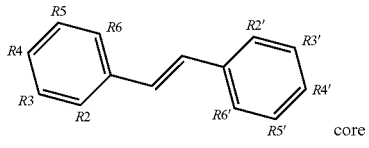

core

Tolans

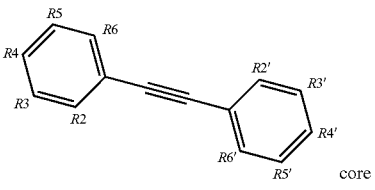

core

| | | |
|---|---|---|
| | 3,4,4'-trihydroxy-3'acetamide-trans-stilbene,<br>3,3'-dihydroxy-4'-acetamide-trans-stilbene, | |
| Azides | 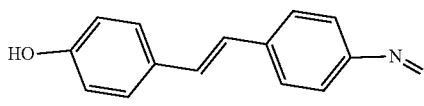<br>4-hydroxy-4'-azidostilbene,<br>3,5-dihydroxy-4'-azidostilbene,<br>4,5-dihydroxy-4'-azidostilbene, or<br>3,4-dihydroxy-4'-azidostilbene,<br>3,4,5-trihydroxy-4'-azidostilbene, | 4-hydroxy-4'-azidotolan,<br>3,5-dihydroxy-4'-azidotolan,<br>4,5-dihydroxy-4'-azidotolan, or<br>3,4-dihydroxy-4'-azidotolan,<br>3,4,5-trihydroxy-4'-azidotolan, |
| Misc. | 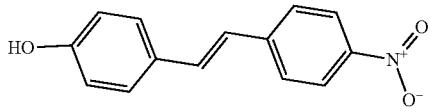 [SMILES: O=[N+]([O-])c1ccc(/C=C/c2ccc(O)cc2)cc1]<br>4-hydroxy-4'-nitro-trans-stilbene, | 4-hydroxy-4'-nitro-tolan, |
| | 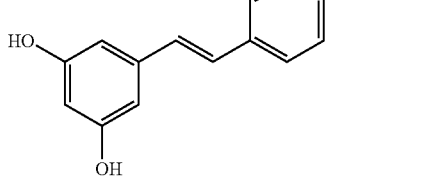<br>3,5-dihydroxy-4'-nitro-trans-stilbene, | 3,5-dihydroxy-4'-nitro-tolan, |
| | 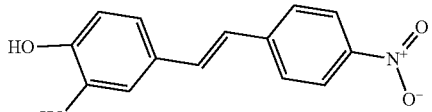<br>3,4-dihydroxy-4'-nitro-trans-stilbene, or<br>4,5-dihydroxy-4'-nitro-trans-stilbene, | 3,4-dihydroxy-4'-nitro-tolan, or<br>4,5-dihydroxy-4'-nitro-tolan, |
| | 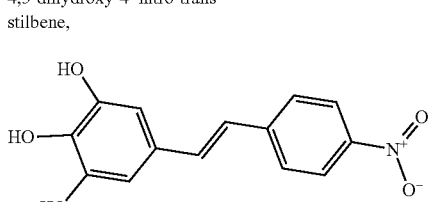<br>3,4,5-trihydroxy-4'-nitro-trans-stilbene | 3,4,5-trihydroxy-4'-nitro-tolan, |

Many of the stilbene compounds are well studied, naturally occurring molecules and some are readily commercially available. Others may be synthesized by routine methods, such as those described by: Ali, M. A., Kondo, K. and Tsuda, Y. (1992). *Synthesis and Nematocidal activity of Hydroxystilbenes*. Chem. Pharm. Bull. 40(5):1130-1136; and Thakkar, K., Geahlen, R. L. and Cushman, M. (1993). *Synthesis and Protein-tyrosine kinase inhibitory activity of polyhydroxylated stilbene analogues of piceatannol*. J. Med. Chem. 36: 2950-2955). Phenyl stilbene derivatives, i.e. those in which at least one $R_a$ or $R_b$ is a phenyl ring, and many other stilbenes may be synthesized according to the methods shown in the dissertation of Zhenlin Bai, *Substituted Stilbenes and 1,2-Diaryl-1,2-diazidoethanes as Potential Anticancer Agents: Syntheses and Estrogenic/Antiestrogenic Properties in MCF-7-2a Cells*, im Fachbereich Biologie, Chemie, Pharmazie der Freien Universität Berlin (2006). Glucoside derivatives may be obtained according to procedures described in WO2007/020673 A1. Tolans may be synthesized using the general procedures described in U.S. Pat. No. 6,599,945 B2 of Docherty & Tsai.

It can be noted that the FAM compounds described above are generally polar, and have certain electronegative substituents (e.g. —OH, —OCH$_3$, —NO$_2$, -halo, —O(C═O)R, etc.) at the respective ends. While this is not deemed essential, it may be desirable to provide for a liquid crystal-like behavior for molecules to assume a lyotrophic or partially ordered structure in solution state.

FAM compounds also include salts of the compounds identified above. FAM compounds, especially those mono or poly-hydroxylated compounds, easily release one or more protons depending on pH to form anions. Such anions may be combined with cations, such as the mono-, di-, and tri-valent cations to form salts. For monovalent cations (M+) a single FAM is linked to form M$^+$FAM$^-$ salts. Similarly, for a divalent cation (M$^{2+}$) two FAM molecules are linked to form M$^{2+}$(FAM$^-$)$_2$ salts; and for a trivalent cation (M$^{3+}$) three FAM molecules are linked to form M$^{+3}$(FAM$^-$)$_3$ salts. The salts are often readily soluble in aqueous media, which may facilitate formulations. Illustrative, but not limiting, cations for FAM salt formation include: Na$^+$ or K$^+$, Mg$^{2+}$, Mn$^{2+}$, Zn$^{2+}$, Ca$^{2+}$, Cu$^+$, Cu$^{2+}$Fe$^{2+}$, and Fe$^{3+}$.

Auxiliary Autophagy Modulators (AAMs) and Formulations

In certain embodiments, the FAM is used in combination with an auxiliary autophagy modulator (AAM). The AMM, when used, may take any of several forms described herein, falling into any of the following classes: vitamins, amino acids, acidic sugars, and quinine derivatives Vitamins Vitamins A, B, C, D, E, and K may all be useful as AAMs. By convention, the term "vitamin" includes neither other essential nutrients, such as dietary minerals, essential fatty acids, or essential amino acids (which are needed in greater amounts than vitamins), nor the great number of other nutrients that promote health. Thirteen vitamins are universally recognized at present. Vitamins are classified by their biological and chemical activity, not their structure. Thus, each "vitamin" refers to a number of "vitamer" compounds that all show the biological activity associated with a particular vitamin. Such a set of chemicals is grouped under an alphabetized vitamin "generic descriptor" title, such as "vitamin A", which includes multiple compounds as described below. Vitamers by definition are convertible to the active form of the vitamin in the body, and are sometimes inter-convertible to one another, as well. In certain embodiments the salt forms of the vitamins, generally without long side aliphatic chains, are excellent AAMs. In certain embodiments, the oxygen containing vitamins are suitable AAMS.

Most vitamins will also form salts that are also within the scope of AAMs. For example, vitamins may combine to form salts with cationic elements like sodium, potassium, magnesium, manganese, calcium, copper, zinc, or iron. Additionally vitamins can form a diethanolamine salt, a 2-amino-2-ethyl-1,3-propanediol salt, a triethanolamine salt, a morpholine salt, a piperazine salt, a piperidine salt, an arginine salt, a lysine salt and a histidine salt. Some vitamins form acetates, palmitates, oleates, linoleates, stearates, lactates, succinates, maleates, citrates, and the like.

Vitamin A refers to a group of lipid soluble, unsaturated, isoprenoid compounds that includes but is not limited to retinol, retinal, retinoic acid, carotenoids, retinyl acetate, retinyl palmitate, α-carotene, β-carotene, γ-carotene, β-cryptoxanthin, xanthophyll, crytoxanthin, 13-cis retinoic acid, 13-trans retinoic acid, tretinoin, ATRA (all trans retinoic acid), lutin, 11-cis-retinal, 11-cis-retinol, 9-cis-retinal, Lecithin, retinyl esters, 9-cis-β-carotene, retinyl palmitate, Acitretin, Vitamin A2 (3,4-dehydroretinol), A3(3-hydroxyretinol), and salts thereof. All isomeric and stereochemical forms of these isoprenoids are encompassed in the invention.

Vitamin B includes but is not limited to the following compounds:

thiamine (B1); riboflavin (B2); niacin or niacinamide (forms of B3); pantothenic acid, panthenol, pantothenol and calcium pantothenate (forms of B5); pyridoxine, pyridoxine 5'-phosphate, pyridoxal, pyridoxal phosphate, pyridoxal 5'-phosphate, pyridoxamine, pyridoxamine 5'-phosphate, 4-pyridoxic acid (forms of B6); biotin, vitamin H or coenzyme R (Forms of B7); Folic Acid, folate, vitamin M, vitamin Bc, pteroyl-L-glutamic acid and pteroyl-L-glutamate, (forms of B9); and Cobalamin, Cyanocobalamin, Hydroxycobalamin, Methylcobalamin, Adenoxylcobalamin (forms of B12); and salts thereof.

Vitamin C refers to ascorbic acid, its anion ascorbate, and salts of ascorbate, as well as ascorbyl palmitate and salts thereof (e.g. ascorbyl palmitate, magnesium ascorbyl palmitate, manganese ascorbyl palmitate, calcium ascorbyl palmitate, zinc ascorbyl palmitate, iron ascorbyl palmitate), benzyl ascorbate, and 2-ascorbyl phosphate.

Vitamin D refers to a group of lipid soluble secosteroid molecules and includes but is not limited to: calcidiol, calcifero (INN), Ergocalciferol and lumisterol (forms of D1); ergocalciferol, fromergosterol, and 25-hydroxy vitamin D$_2$ (forms of D2); Cholecalciferol, 7-dehydrocholesterol, and 25-hydroxycholecalciferol (or 25-hydroxyvitamin D$_3$, abbreviated 25(OH)D$_3$, (forms of D3); 22-dihydroergocalciferol (D4); Sitocalciferol, 7-dehydrositosterol (D5); 25-D-glucuronic acid, 25-D-hexuronic acid, 25-hydroxy vitamin D$_2$-25-β-D-glucuronide, and salts thereof.

Vitamin E refers to a group of lipid soluble compounds that are either tocopherols or tocotrienols, the most active of which is α-tocopherol. Other tocopherols include, beta, gamma, delta. Similarly, tocotrienols exist in alpha, beta, gamma and delta forms as well. All isomeric and stereochemical forms of these tocopherols and tocotrienols and their salts are encompassed in the invention. For example, synthetic vitamin E is a mixture of eight isomeric forms, usually labeled "all-rac" or "dl." Tocopherol and tocotrienol derivatives include all R and all S stereoisomers of tocopherols (RRR, RRS, RSR, SRR, RSS, SRS and SSS) and the two stereoisomers of tocotrienols (e.g. R or S-α-tocotrienols). Other examples include: Conjugated vitamin E molecules; vitamin E or tocopherol or tocotrienol esters; alpha-tocopheryl acetate; vitamin E esters (e.g. alpha-tocopheryl succinate) include a group of compounds formed by esterifying a vitamin E molecule with a carboxylic acid; d-α-tocopherol is often a mixture of two or more enantiomers of other tocopherols (β,γ,δ,ε,ζ,η) or as tocotrienols, n-propionate or linoleate such as vitamin E acetate or alpha-tocopheryl acetate. Water soluble forms of vitamin E include: Magnesium R-(+)-alpha lipoate, 6-hydroxy-2,5,7, 8-tramethylchroman-2-carboxylic acid (trolox), or salts of vitamin E Vitamin K refers to a group of compounds having a 2-methyl-1,4,naphthoquinone core and a side chain at the 3 position. Vitamers $K_1$ (phylloquinone, phytomenadione, or phytonadione) and $K_2$ (menaquinones) are naturally occurring. In fact, $K_2$ is not one, but a series of compounds having varying-length isoprenoid side chains; and the menaquinone family is sometimes designated MK-n, where n is the number of isoprenoid groups, n=4 being the most common. In addition, some synthetic vitamin K analogs have been made, including $K_3$ (menadione) which has no side chain, $K_4$, $K_5$ (2-methyl-4-amino-1-naphthol hydrochloride), vitamin $K_6$ (2-methyl-1,4-naphthalenediamine) and $K_7$. Many vitamin K compounds form salts and the divalent salts are most useful as AAMs. For example, salts of a cations may take the form: $M(Ki)_2$ where M is a divalent cation or $M(Ki)_3$ where M is a trivalent cation. In certain embodiments, useful AAMs include salt dimers of vitamin K and a divalent cation like Ca or Mg.

Vitamin P (although a somewhat outdated term) refers to a group of flavonoids, having the general structure of a 15-carbon skeleton, which consists of two phenyl rings (A and B) and heterocyclic ring (C). This carbon structure can be abbreviated C6-C3-C6. Based on the nature of the substituents and position on the skeleton, flavonoids fall into one of three chemical classes: (1) flavonoids or bioflavonoids based on the flavone core (2-phenyl-1,4-benzopyrone); (2) isoflavonoids based on the a 3-phenylchromen-4-one (3-phenyl-1,4-benzopyrone) core structure; and (3) neoflavonoids, based on a 4-phenylcoumarine (4-phenyl-1,2-benzopyrone) core structure.

Amino Acids

Certain amino acids and their derivatives are also useful as AAMs. As is well known, and amino acid has the general formula

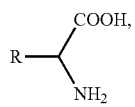

where R is any of several well understood side chains. There are 20 amino acids coded by generic codes and humans synthesize 11 of these, making the other 9 "essential" amino acids, which must be consumed in the diet. The 20 are: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine. All isomeric and stereochemical forms of these amino acids, and salts of these amino acids, are encompassed in the invention. In certain embodiments, useful amino acids include but are not limited to: tyrosine, phenylalanine, cysteine, serine, threonine, and tryptophan. Additionally certain amino acid derivatives are useful, for example lycopene and N-actylcysteine (NAC)

Acidic Sugars

Acidic sugars include mono-, and di-saccharides formed from 4 to 6-member aldoses and ketoses. They are generally acidic due to the readiness with which a proton is released from the many hydroxyl groups. Useful monosaccharides, include but are not limited to erythrose, erythulose, threose, ribose, ribulose, arabinose, xylose, xylulose, glucose, dextrose (or D-glucose), mannose, glactose, fructose, and sorbose. Useful disaccharides include but are not limited to maltose, sucrose, lactose, cellobiose and trehalose. All isomeric and stereochemical forms of these sugars are encompassed in the invention.

Quinone Derivatives

Quinone derivatives include those having 1, 2 or three rings, therefore including 1,4-benzoquinones based on

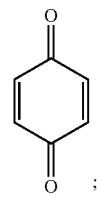

1,4-naphthoquinones based on

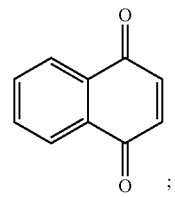

9,10-anthraquinones based on

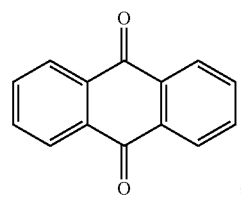

and 1,3 indandiones based on

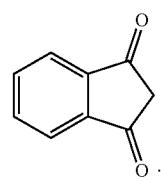 [SMILES: O=C1CC(=O)c2ccccc21]

These quinone derivatives may contain substituents at any position other than the ketones, the substituents generally being selected from hydroxyl, methoxy, methyl, ethyl, halo, and amino. From 1-4 hydroxyl substituents are particularly useful. For example, other examples of hydroxy-1,4-benzoquinone derivatives include 2-hydroxy-1,4-benzoquinone, 2,3-dihydroxy-1,4-benzoquinone, 2,5-dihydroxy-1,4-benzoquinone, 2,6-dihydroxy-1,4-benzoquinone, 2,3,5-trihydroxy-1,4-benzoquinone, and 2,3,5,6-Tetrahydroxy-1,4-benzoquinone. Other 1,4-benzoquinone derivatives include: 2,6-Dimethoxy-1,4-benzoquinone, 2,3,5,6-Tetramethyl-1,4-benzoquinone, 1,4-benzoquinonetetracarboxylic acid, blatellaquinone, 2,5-Dichloro-3,6-dihydroxybenzoquinone (chloranilic acid), and 2-Isopropyl-5-methylbenzo-1,4-quinone (thymoquinone).

Examples of mono-, di-, and tetra-hydroxy-1,4-naphthoquinones include 2-hydroxy-1,4-naphthoquinone (lawsone), 5-hydroxy-1,4-naphthoquinone (juglone), 6-hydroxy-1,4-naphthoquinone, 2,3-dihydroxy-1,4-naphthoquinone, 2,5-dihydroxy-1,4-naphthoquinone, 2,6-dihydroxy-1,4-naphthoquinone, 2,7-dihydroxy-1,4-naphthoquinone, 2,8-dihydroxy-1,4-naphthoquinone, 5,6-dihydroxy-1,4-naphthoquinone, 5,7-dihydroxy-1,4-naphthoquinone, 5,8-dihydroxy-1,4-naphthoquinone (naphthazarin), 6,7-dihydroxy-1,4-naphthoquinone, and 2,3,5,7-tetrahydroxynaphthoquinone (spinochrome B). Other 1,4-naphthoqinone derivatives include menadione (sometimes referred to as Vitamin K3 or 2-methyl-1,4-naphthoquinone).

Examples of 9,10 anthraquinolones include the dihydroxy derivatives 1,2-Dihydroxyanthraquinone (alizarin), 1,3-Dihydroxyanthraquinone (purpuroxanthin, xantopurpurin), 1,4-Dihydroxyanthraquinone (quinizarin), 1,5-Dihydroxyanthraquinone (anthrarufin), 1,6-Dihydroxyanthraquinone, 1,7-Dihydroxyanthraquinone, 1,8-Dihydroxyanthraquinone (dantron, chrysazin). 2,3-Dihydroxyanthraquinone, 2,6-Dihydroxyanthraquinone, and 2,7-Dihydroxyanthraquinone; the trihydroxy-derivatives 1,2,3-Trihydroxyanthraquinone (anthragallol), 1,2,4-Trihydroxyanthraquinone (purpurin), 1,2,5-Trihydroxyanthraquinone (oxyanthrarufin), 1,2,6-Trihydroxyanthraquinone (flavopurpurin), 1,2,7-Trihydroxyanthraquinone (isopurpurin, anthrapurpurin), 1,2,8-Trihydroxyanthraquinone (oxychrysazin), 1,3,5-Trihydroxyanthraquinone, 1,3,6-Trihydroxyanthraquinone, 1,3,7-Trihydroxyanthraquinone, 1,3,8-Trihydroxyanthraquinone, 1,4,5-Trihydroxyanthraquinone, 1,4,6-Trihydroxyanthraquinone, 1,6,7-Trihydroxyanthraquinone, and 2,3,6-Trihydroxyanthraquinone.

Salt complexes may be formed of FAM and/or AAM compounds as has already been described. In addition, complexes may also be formed between FAM compounds and certain AAM compounds. Such FAM+AAM complexes include at least those with vitamins, such as ascorbates and ascorbylpalmitates; those with amino acids, such as arginates, lysinates, aspartates, glutamates; and those with acidic sugars, such as glucosides, ribosides, galactosides, mannosides, and the like. Example 4 provides a few concrete examples of both salts and complexes of FAM and AAM compounds.

The nature of the FAM compounds as liquid crystals may facilitate and/or mediate their role in wound healing. The polar nature of the liquid crystals allows them to self assemble into polymeric-like structures; they are thus capable of (i) generating their own hydrogels, and/or, (ii) by addition of these molecules to traditional hydrogels, enhancing the sol-gel transition state to create a unique set of liquid crystal hydrogels. These gels may be modified to create any variety of the aforementioned gel types from strong to weak chemical bonding or the creation of a biodegradable gel. Without wishing to be bound by any particular theory, it is believed that these FAM molecules are useful in wound healing applications, in part because the molecules themselves can behave like the collagen fibrils that assemble higher order structures to help with scaffolding and cell migration during wound healing. Further, addition of these liquid crystal hydrogels may facilitate proper collagen alignment and orientation reducing the risk of scar or keloid formation during the wound healing process.

In addition to hydrogel formulations, another useful formulation of FAM compounds is with cyclodextrins. A general cyclodextrin formula consists of an FAM with a ratio of FAM:Cyclodextrin of about 1:1, 1.5:1, 1.5:2, 1.5:3, 1:3, 1.5:4, 1:4, 1.5:5, 1:5, 1.5:6, 1:6, 1.5:7, 1:7, 1.5:8, 1:8, 1.5:9, 1:9, 1.5:10 or 1:10. These ratios will allow for adequate dissolving of the FAM in cyclodextrin. An AAM may be added from about 0.1% to about 99% (w/v), e.g. 0.1-10%, 10-20%, 20-30%, 30-40%, 50-60%, 60-70%, and 80-90% (w/v) or higher.

Utility of FAMs and AAMs in Autophagy Modulation

Figure 2:
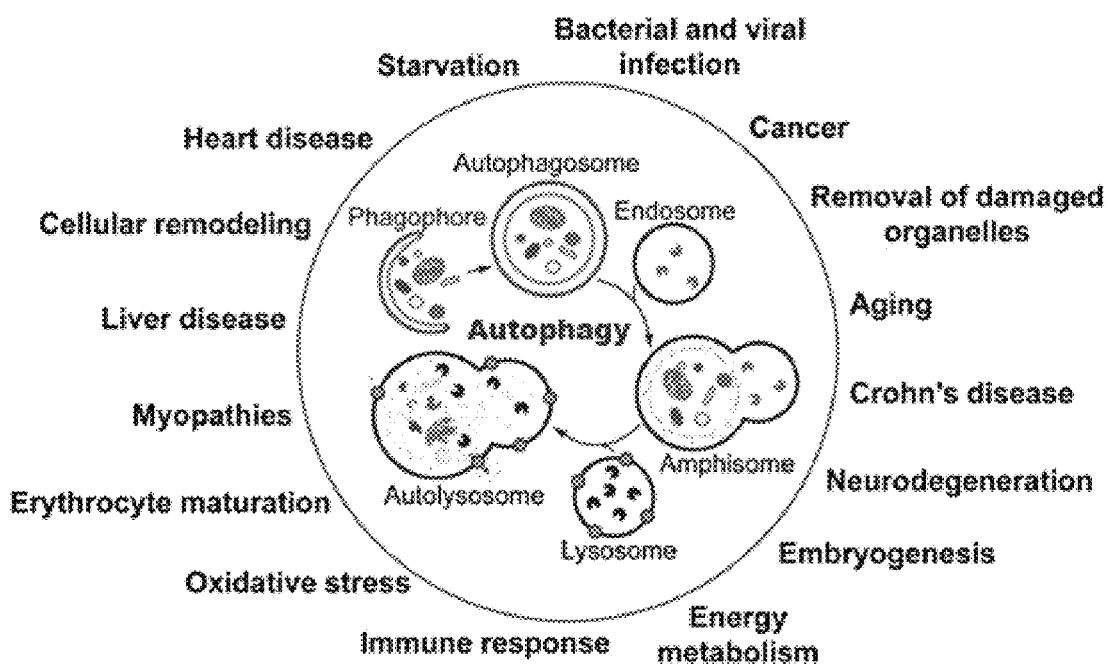
FIG. 2 is a schematic illustration showing autophagy related human diseases.

In recent years, scientists have been studying the effects of the regulation of the autophagy pathways as a way to treat a variety of serious illnesses. In fact, dysregulation of autophagy has been linked to major diseases including heart disease, cancer and diabetes (See FIG. 2, taken from Klionsky D. J. (2010). The Autophagy Connection. Developmental Cell. July 20; 19(1):11-2.) This paper describes the link between the autophagy pathways and major human diseases. While not naming individual "myopathies," the ability to regulate this pathway is a major link to modulating disease outcomes. Depending on the disease state it may be beneficial to upregulate or downregulate cellular levels of autophagy.

In some disease states, the pathological origins are related to suppressed autophagic activity or the activation of autophagy and its related signaling pathways will result in the suppression of inflammation. Hence, diseases or conditions where it may be beneficial to upregulate autophagy include: wound healing, promote hair regrowth, bacterial infections, inflammation, viral infection, Parkinson's disease, Alzheimers, neurodegenerative diseases, neuropathy, cardiovascular disease, heat failure, heart disease, aging, Alzheimer's disease, atherosclerosis, arterosclerosis, chronic obstructive pulmonary disease (COPD), Crohn's disease, inflammatory bowel, colitis, diabetes, diabetes type I and II, amyloidosis, bursitis, dermatitis, angitis, autoimmune diseases with inflammation, blood diseases, aplastic anemia, endometriosis, hepatitis, herpes, HIV, multiple sclerosis, retinal detachment, age-related macular degeneration, retinitis pigmentosa, and Leber's congenital amaurosis, lysosomal storage diseases, arthritis, psoriasis, osteopenia, osteoporosis, surgical scars, surgical adhesions, space travel (bone density disorder), tendonitis, and ulcerative colitis.

In other disease states the pathological origins are related to overexpression of autophagic activity and the activation of autophagy and its related signaling pathways. Hence, diseases or conditions where it is beneficial to downregulate autophagy include: Aging, Cancer, polycystic kidney and liver disease, kidney disease, liver disease, asthma, diabetic retinopathy, fibromyalgia, ankylosing spondylitis, celiac disease, Grave's disease, lupus, metabolic diseases, nephritis, rheumatoid arthritis, osteolysis, ischemia-reperfusion (I/R) injury, organ and tissue transplant, scleroderma, and sepsis.

In wound healing, increasing autophagy levels assists in tissue protection, decreases inflammation and promotes the synthesis of procollagen, hyaluronan and elastin. As shown herein FAM and AAM compounds have been used alone and in combination to promote wound healing, hair growth, and skin repair following damage from UV radiation exposure.

In bacterial infections various types of bacteria attempt to interfere with the autophagy pathway to prevent the cellular uptake of the bacteria ultimately leading to autophagolysome degradation of the bacteria. Two clinically important skin pathogens, *Streptococcus* sp. and *Staphylococcus aureus* interfere with the autophagy pathway (see, I. Nakagawa, et al, *Autophagy defends cells against invading group A Streptococcus*, Science 306, 1037-1040 (2004); and Schnaith, et al, *Staphylococcus aureus subvert autophagy for induction of caspase-independent host cell death*, J BiolChem 282, 2695-2706 (2007). Invasive skin infections with group A *Streptococcus* are characterized by the prevention of cellular uptake of bacteria due to encapsulation; and if bacteria are taken up by keratinocytes, the majority of streptococci are killed within a few hours (H. M. Schrager, J. G. Rheinwald and M. R. Wessels: *Hyaluronic acid capsule and the role of streptococcal entry into keratinocytes in invasive skin infection*, J Clin Invest 98, 1954-1958 (1996)). Nakagawa et al. (cited above) showed that autophagy is responsible for the killing activity. Although, some bacteria survive, the reduction of the number of extracellular streptococci is likely to have a partially protective effect. As the mechanistic studies of the action of autophagy against group A *Streptococcus* have not been performed in keratinocytes, additional studies will be necessary to understand the relevance and efficiency of this putative antibacterial strategy in the skin. *S. aureus* induces autophagy via its alpha-toxin (Schnaith et al, above, and M. B. Mestre, C. M. Fader, C. Sola and M. I. Colombo: *Alpha-hemolysin is required for the activation of the autophagic pathway in Staphylococcus aureus-infected cells*, Autophagy 6, 110-125 (2010)). Pore-forming toxins cause a drop in nutrient and energy levels that trigger autophagy as a rescue mechanism to re-establish cellular homoeostasis (N. Kloft, et al: *Pro-autophagic signal induction by bacterial pore-forming toxins*, Med Microbiolmmunol 199, 299-309 (2010)). Whether autophagy suppresses or enhances *S. aureus* infection in the skin in vivo remains to be determined.

EXAMPLES

Example 1: Synthesis of Certain FAMs of the invention: The following compounds were prepared and given identifying numbers as shown in Table B.

TABLE B

Stilbene and Tolan compounds useful in the invention

| Identifier | Compound Name | Structure |
|---|---|---|
| BM2201 | 4,4'-dihydroxy-trans-stilbene | 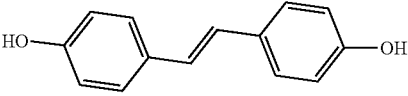 |
| BM2301 | 3,5,4'-trihydroxy-trans-stilbene | 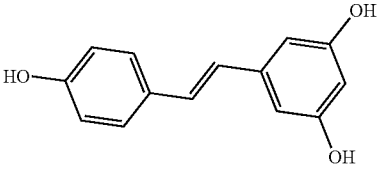 [SMILES: Oc1ccc(/C=C/c2cc(O)cc(O)c2)cc1] |
| BM2401 | 3,3',5,5'-tetrahydroxy-trans-stilbene | 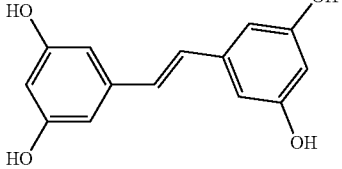 |
| BM2213 | 4-hydroxy-4'-(trifluoro)methyl-trans-stilbene | 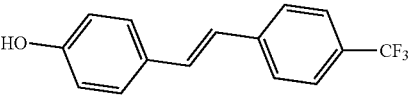 [SMILES: Oc1ccc(/C=C/c2ccc(C(F)(F)F)cc2)cc1] |
| BM3103 | 4-hydoxy-4'-methoxytolan | 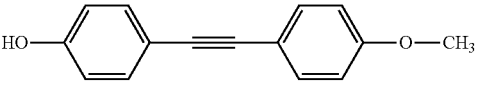 |
| BM3302 | 2,4,4'-trihydroxytolan | 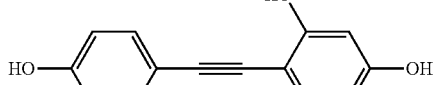 |
| BM3032 | 2,4,4'-trimethoxytolan | 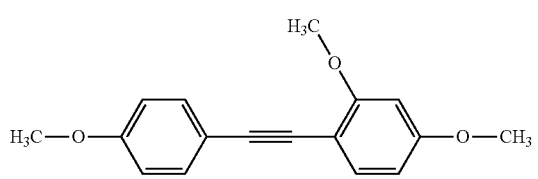 |

TABLE B-continued

Stilbene and Tolan compounds useful in the invention

| Identifier | Compound Name | Structure |
|---|---|---|
| BM3203 | 4,4'-dihydroxy-3-methoxytolan | 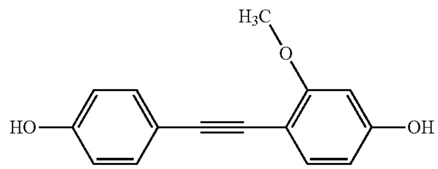 [SMILES: COc1cc(O)ccc1C#Cc1ccc(O)cc1] |
| BM3402 | 2,4,2',4'-tetrahydroxy-tolan | 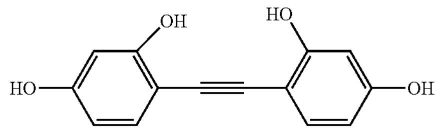 [SMILES: Oc1ccc(C#Cc2ccc(O)cc2O)c(O)c1] |
| BM3206 | 4,4'-dihydroxytolan-2-O-β-D-glucoside | 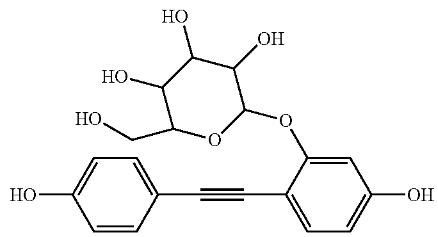 [SMILES: OCC1OC(Oc2cc(O)ccc2C#Cc2ccc(O)cc2)C(O)C(O)C1O] |
| BM3301 | 3,5,4'-trihydroxytolan | 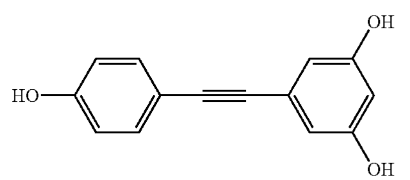 [SMILES: Oc1ccc(C#Cc2cc(O)cc(O)c2)cc1] |
| BM3401 | 3,3',5,5'-tetrahydroxytolan | 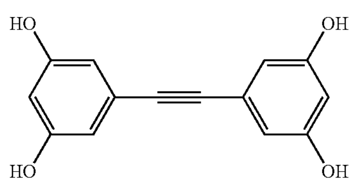 [SMILES: Oc1cc(O)cc(C#Cc2cc(O)cc(O)c2)c1] |
| BM3213 | 4-hydroxy-4'(trifluoro)methyltolan | 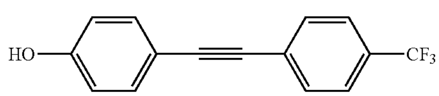 [SMILES: Oc1ccc(C#Cc2ccc(C(F)(F)F)cc2)cc1] |

Stilbene compounds (BM2xxx series) were synthesized/obtained according to the procedures described in Ali, M et al 1992, and Thakkar, K. et al 1993, noted above. Tolan compounds (BM3xxx series) were synthesized according to the procedures described in U.S. Pat. No. 6,599,945 B2 of Docherty & Tsai.

Example 2: Simplified synthesis procedures for 4-hydroxy-4' methoxytolan

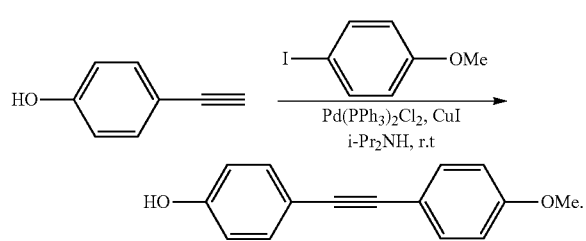

Synthesis Procedure for 4-Hydroxy-4'-methoxytolan(4-((4'-methoxyphenyl)ethynyl)phenol) was a Heck-type reaction modified from (Pavia, M. R.; Cohen, M. P.; Dilley, G. J.; Dubuc, G. R.; Durgin, T. L.; Forman, F. W.; Hediger, M. E.; Milot, G.; Powers, T. S.; Sucholeiki, I.; Zhou, S.; Hangauer, D. G. The design and synthesis of substituted biphenyl libraries. Bioorg. Med. Chem. 1996, 4, 659-666., Jeffery, T. Heck-type reactions in water. *Tetrahedron Lett,* 1994, 35, 3051-3054, Jeffery, T.; Galland, J. C. *Tetraalkylammonium salts in heck-type reactions using an alkali metal hydrogen carbonate or an alkali metal acetate as the base. Tetrahedron Lett,* 1994, 35, 4103-4106, and Schmidt-Radde, R. H.; Vollhardt, K.; Peter C. The total synthesis of angular [4]- and [5] phenylene *J Am Chem Soc,* 1992, 114, 9713-9715). The resulting product was a yellowish powder and was verified using $^1$HNMR (CDCl$_3$, 300 MHz): δ ppm: 7.44 (d, 4H, J=8.7, Ar—H), 6.89 (d, 2H, J=8.7, Ar—H), 6.82 (d, 2H, J=8.7, Ar—H), 4.89 (s, 1H, OH), 3.85 (s, 3H, CH$_3$O). The resulting product was 98.2% pure and was used for all subsequent testing.

Example 3: Synthesis Procedure outline for 2,4,4'-trimethoxytolan: Synthesis was a Heck-type reaction analogous to that of Example 2.

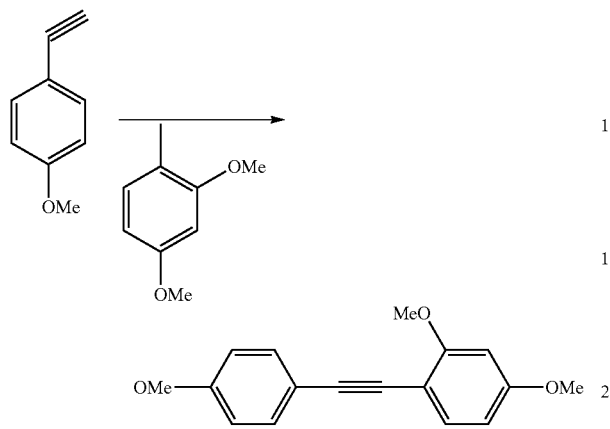

The resulting product was an off white powder and was verified using ¹HNMR (CDCl₃, 400 MHz): δ ppm: 7.47 (d, 2H, J=6.4, Ar—H), 7.40 (s, 1H, Ar—H), 6.85 (d, 2H, J=6.8, Ar—H), 6.47 (dd, 2H, J=2.4, Ar—H), 3.89 (s, 3H, CH₃O), 3.82 (s, 6H, 2CH₃O) and found to be 99.3% pure.

Example 4: Melting points of FAM salts and FAM and AAM salt complexes: All salts were made by combining sufficient quantities of each stilbene, tolan or combination with magnesium hydroxide, zinc oxide, ascorbic acid or ascorbyl palmitate to generate a salt solution. Each solution was then dried in 20 mL scintillation vials using a rotary evaporator (Centrifan, Harvard Biosciences) set to 40° C. and evaporated with a mixture of ethanol and ice to allow for a slower evaporation. Once evaporated and dried completely the salts were ground into a fine powder and their melting points were used to confirm the formation of the salt. Melting points (Table C, below) were determined using a Meltemp II apparatus outfitted with a temperature probe and thermal couple to provide a digital read out. Apparatus was calibrated and compounds with known melting points were tested to confirm calibration prior to analysis of unknowns.

TABLE C

| Melting points | |
|---|---|
| FAM's | Melting Point |
| 4-hydroxy-4'-methoxytolan | 140-144° C. |
| 3,5,4' trihydroxytolan | 208-214° C. |
| 3,5,3',5'tetrahydroxystilbene | 319-322° C. |
| 2,4,4' trimethoxytolan | 68-73° C. |
| FAM complexes | |
| Mg-4-hydroxy-4'-methoxytolan | 150-152° C. |
| Mg-3,5,4' trihydroxytolan | 222-232° C. |
| Mg-3,5,3',5' tetrahydroxystilbene | 324-337° C. |
| Mg-2,4,4' trimethoxytolan | 71-76° C. |
| Zn-3,5,4' trihydroxytolan | 161-164° C. |
| Zn-3,5,3',5'tetrahydroxystilbene | 217-221° C. |
| Zn-2,4,4' trimethoxytolan | 69-73° C. |
| Zn-4-hydroxy-4'-methoxytolan | 168-173° C. |
| FAM + AAM complexes | |
| Mg-Ascorbate-4-hydroxy-4'-methoxytolan | 173-183° C. |
| Zn-Ascorbate-4-hydroxy-4'-methoxytolan | 168-175° C. |

TABLE C-continued

| Melting points | |
|---|---|
| FAM's | Melting Point |
| AAM's | |
| Ascorbic Acid | 190-192° C. |
| Mg(OH)₂ | 350° C. |
| ZnO | 1975° C. |
| Ascorbyl Palmitate | 115-116° C. |

Figure 3:
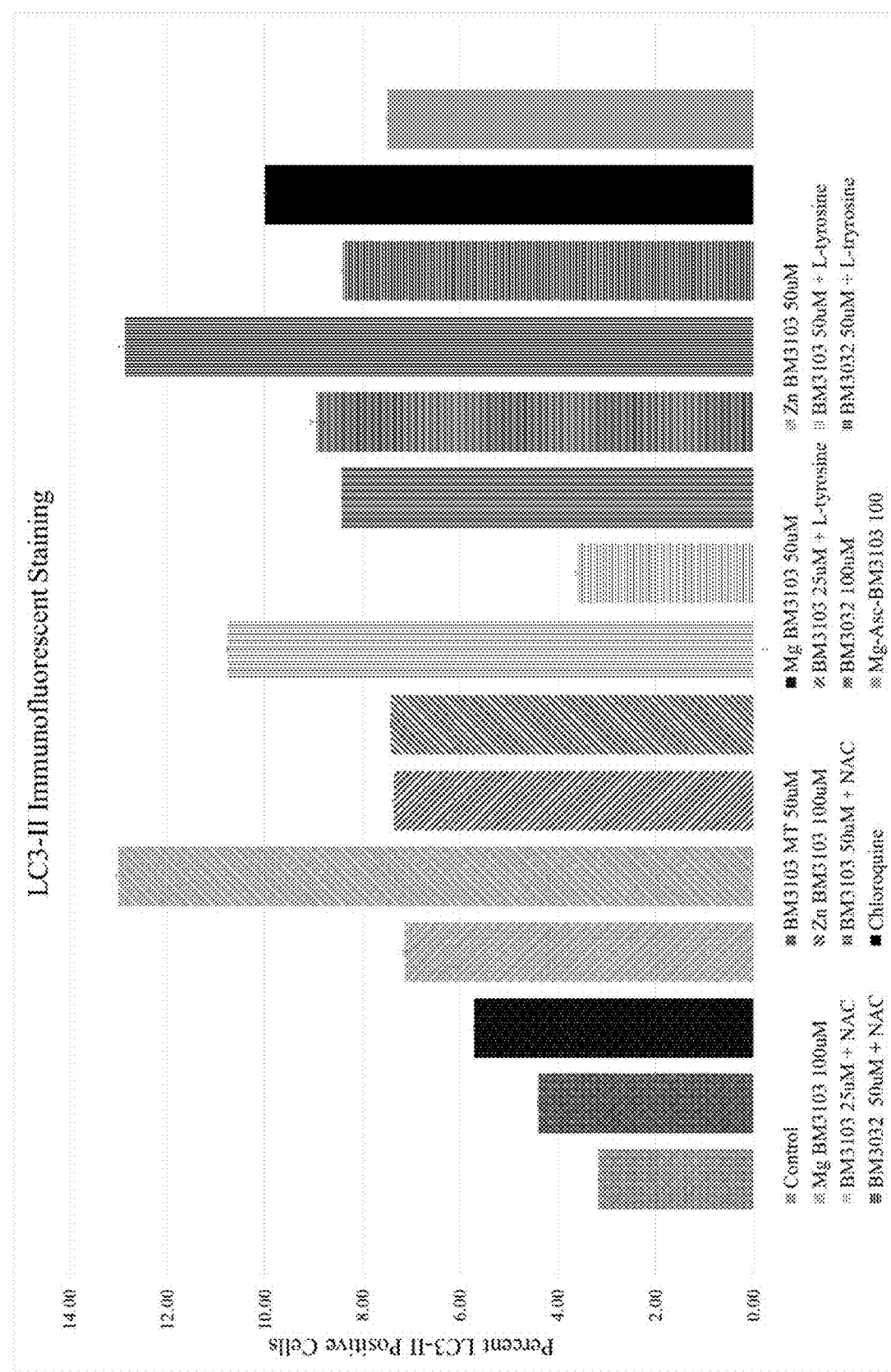
FIG. 3 is a bar graph of LC3-II fluorescent staining as described in Example 5.

Example 5: LC3-II (microtubule associated protein 1 light chain 3) staining in human dermal fibroblasts: Staining method was modified from procedures described by: Furuta, S, (2000) *Ras is involved in the negative control of autophagy through the class I PI3-kinase*, Oncogene. 23: 3898-3904; Ge, J. N. et al, (2008) *Effect of starvation-induced autophagy on cell cycle of tumor cells*, Chinese Journal of Cancer27:8 102-108; and Settembre, C. et al (2011) *TFEB Links autophagy to lysosomal biogenesis*, Science 332:17 1429-1433. HDFn (Human dermal fibroblasts neonatal, ThermoFisher) cells were seeded at 5,000 cells/well into a black well clear bottom plate (Coning, Corning, N.Y.). Cells were then treated with media alone, FAM, AAM or combination thereof for 8 hrs. Following treatment time(s) the cells were fixed with 4% (w/v) PFA (paraformaldehyde) at room temperature for 15 min. Cells were then washed with PBS (phosphate buffered saline, pH 7.4) and blocked with 5% (w/v) BSA in PBS for 1 hr. Cell were washed again with PBS and incubated in primary antibody for LC3-IIB (rabbit monoclonal antibody, Thermo-Fisher) for 3 hrs. Cells were rinsed again in PBS and the secondary fluorescent antibody (Alexafluor 488 rabbit anti goat, ThermoFisher) was added for 30 minutes. The plates were then imaged using the SpecraMax i3X (Molecular Devices, Sunnyvale, Calif.) and SoftMax Pro 6.5.1 software was used to determine the number of LC3-II positive cells. Results are shown in FIG. 3

Figure 4:
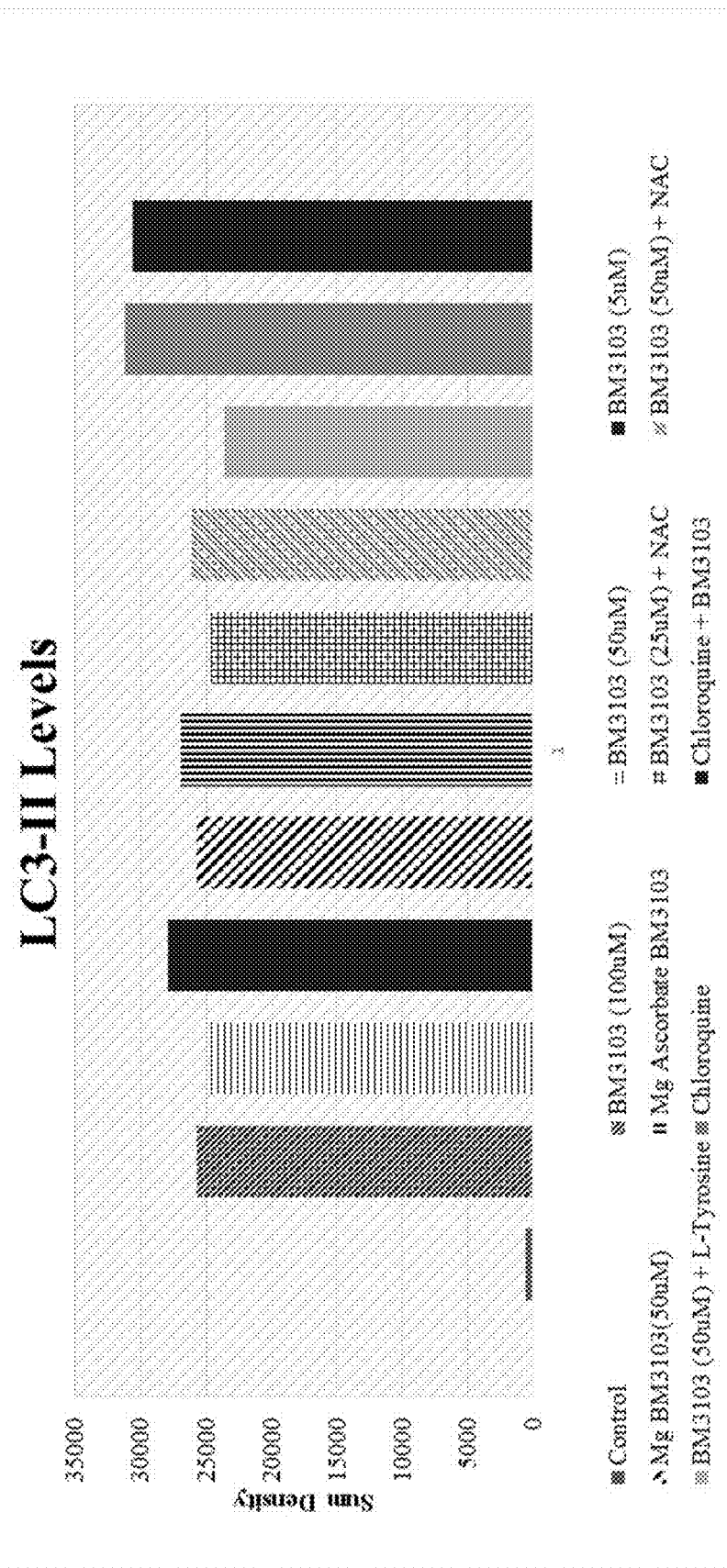
FIG. 4 is a bar graph of an LC3-II Western Blot as described in Example 6.
Figure 5:
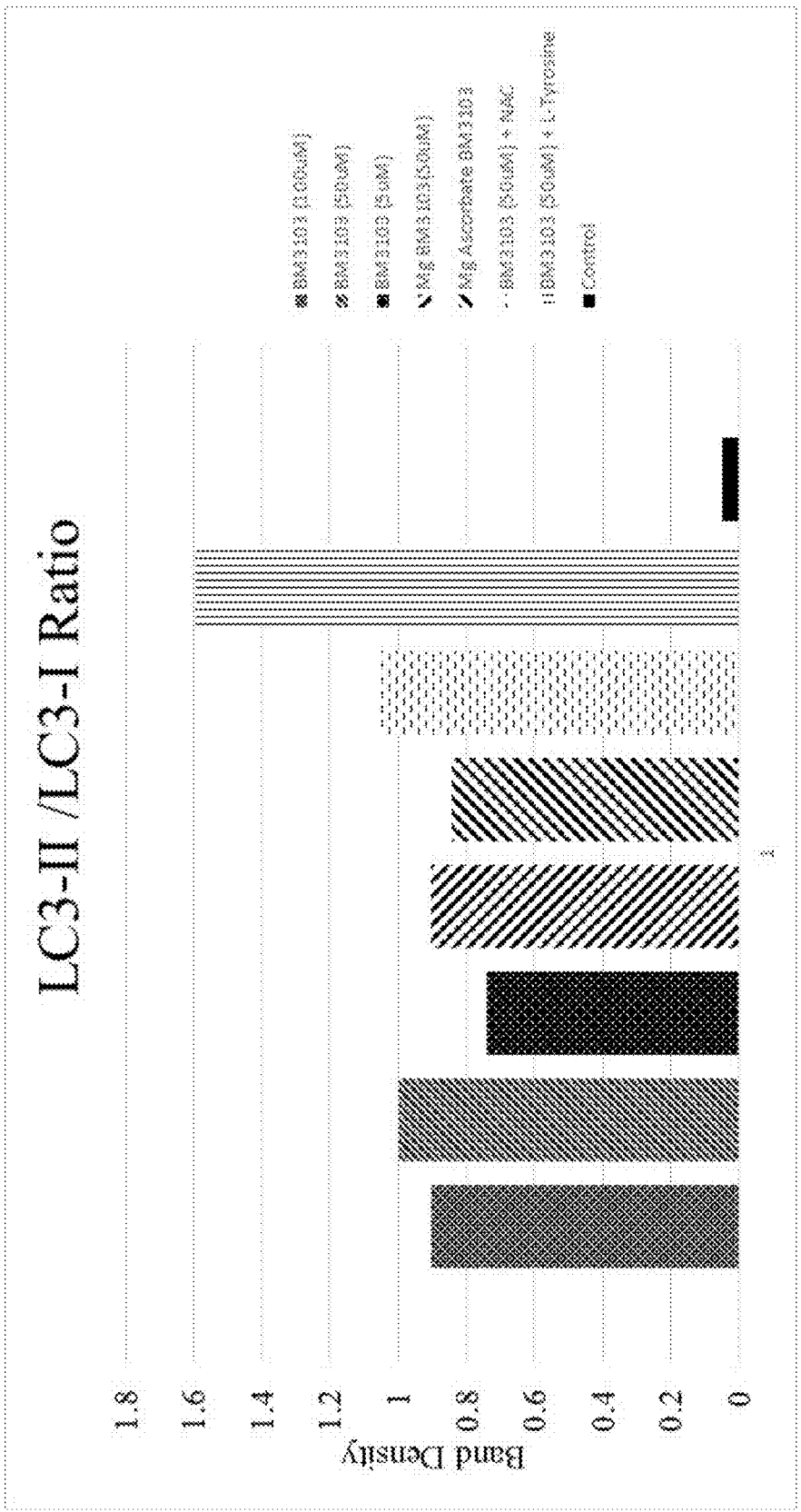
FIG. 5 is a bar graph of the LC3-II/LC3-I ratio as described in Example 6.

Example 6: Autophagy modulation and hormesis: LC3-II Western blot: Human dermal fibroblasts were plated at a density of 1×10⁶ cells per T25 tissue culture treated flasks. Cells were then treated with an FAM, AAM or combination for 8 hrs. Cells were then trypsinized, washed with 1×PBS and lysed with RIPA buffer+protease inhibitor on ice. Cells were sonicated and a BCA protein assay (Pierce Scientific) was run to determine protein concentrations. Concentrations were then normalized to 100 ug per sample and run on a 12% (w/v) polyacrylamide gel with loading dye and appropriate molecular weight markers (All reagents were purchased from National Diagnostics). The gel was then transferred, blocked and a primary monoclonal antibody to MAPLC3-2 (Thermo-Fisher) was added to the membrane and allowed to incubate overnight. Following appropriate washing a Eu-labeled secondary antibody (Molecular Devices) was added and the membrane was imaged using the Spectramax i3x equipped with the Scan Later module. The gel was subsequently stripped and re-probed for actin to confirm appropriate loading. SoftMax Pro 6.5.1 software was used to determine changes in average band intensity. Results are shown in FIGS. 4 & 5.

Example 7: Autophagy, Wound Healing and the Skin: Very low levels of autophagy are present in the skin, functioning to degrade protein aggregates, damaged organelles and to effect skin color through an FGF-PI3K-AKT-MTOR signaling pathway in the melanosomes (Belleudi, et al. *The receptor tyrosine kinase FGFR2b/KGFR controls* early differentiation of human keratinocytes, PLoS One 2011; 6:e24194; PMID:21957444; http://dx.doi.org/10.1371/journal.pone.0024194; and Belleudi, et al, *Expression and signaling of the tyrosine kinase FGFR2b/KGFR regulates phagocytosis and melanosome uptake in human keratinocytes*. FASEB J 2011; 25:170-81; PMID:20844240; http://dx.doi.org/10.1096/fj.10-162156.) The induction of autophagy in human kertinocytes negatively regulates p62, preventing excessive inflammation and induction of cathelicidin (found in the lysosomes of macrophage and PMN's). (Lee, et al *Autophagy Negatively Regulates Keratinocyte Inflammatory Responses via Scaffolding Protein p62/SQSTM*1. J Immunol. published online 15 Dec. 2010). In a deep wound second degree burn model the autophagy inducer rapamycin was shown to enhance autophagic vesicle formation, improve wound reepithelization times and decreased IL-8, methane dicarboxylic aldehyde (MDA an indicator of oxidative stress) and myeloperoxidase (an indicator of the production of hypochlorous acid (HOCl), hydrogen peroxide ($H_2O_2$) and chloride anions (Cl—)) levels. (Xiao et al, (2013) *Rapamycin reduces burn wound progression by enhancing autophagy in deep second-degree burn in rats*. Wound Rep. Reg. 21: 852-859). This indicates that the induction of autophagy in the skin creates an anti-inflammatory effect. Rapamycin is a known hormetic chemical that, when used in a dose dependent fashion, can prevent or treat a variety of diseases.

The formulations described in this patent are hormetic substances that have been shown to induce autophagy in a dose dependent fashion for the treatment of a variety of diseases and medical conditions, including increased wound closure and re-epitheliazation, as shown below.

Figure 6:
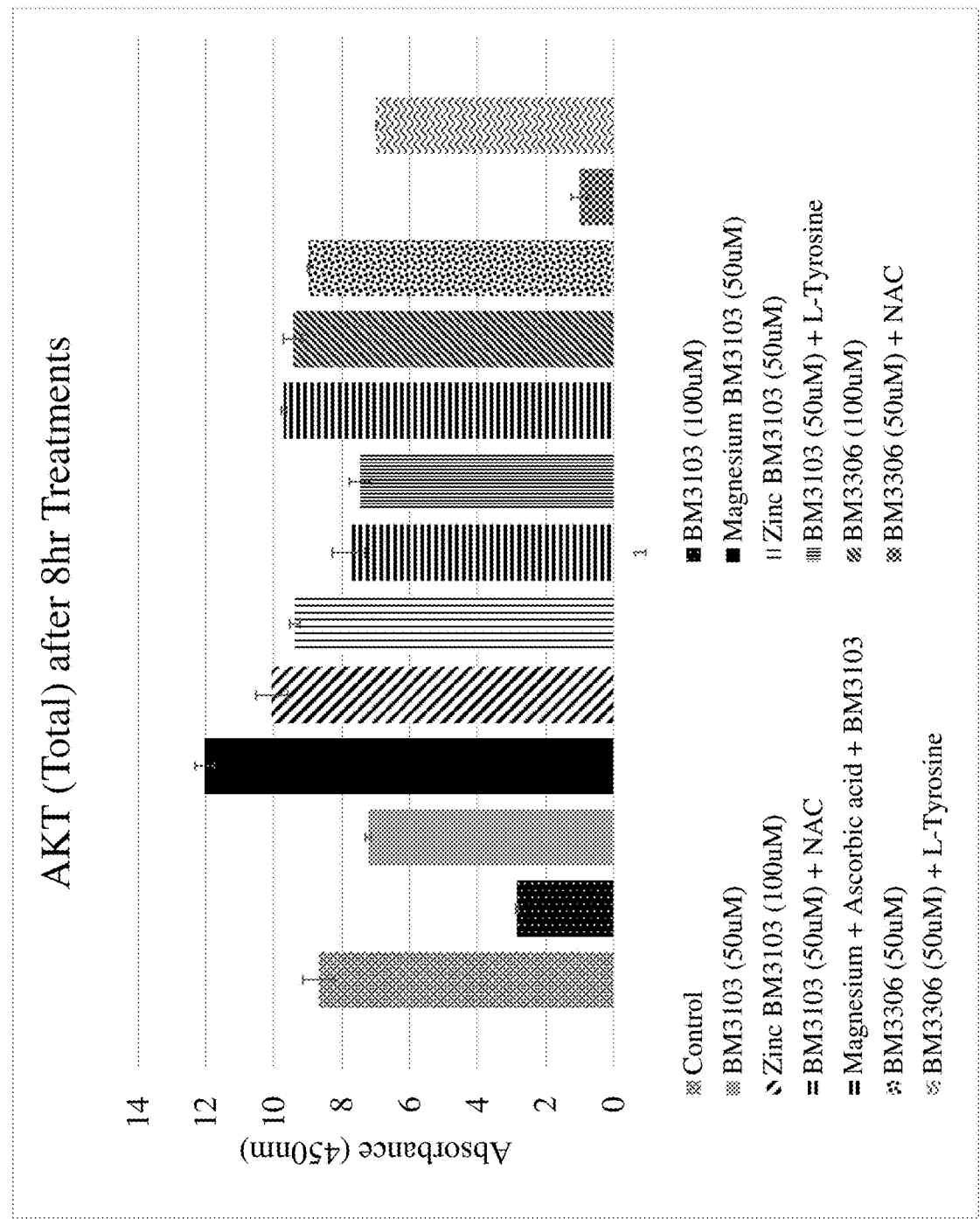
FIG. 6 is a graph of AKT signaling as described in Example 8.

Example 8: Protein Kinase B (AKT): HDFn cells were plated in T-25 flasks at a density of $1 \times 10^6$ cells per flasks and allowed to attach and spread overnight. Cells were then treated for 8 hrs with Control media, FAM, AAM or combination. Cells were removed using trypsin, followed by trypsin neutralizer and spun down to collect cell pellet. Cells were washed in ice cold 1×PBS and then lysed with RIPA buffer+protease inhibitor on ice. Samples were spun down, aliquoted and frozen until they could be assayed using an ELISA. Cells were sonicated and diluted 1:5 as recommended in kit instructions. Samples were then assayed using an AKT ELISA (Thermo-Fisher) and concentrations were determined using an AKT standard curve. Results are shown in FIG. 6.

Figure 7:
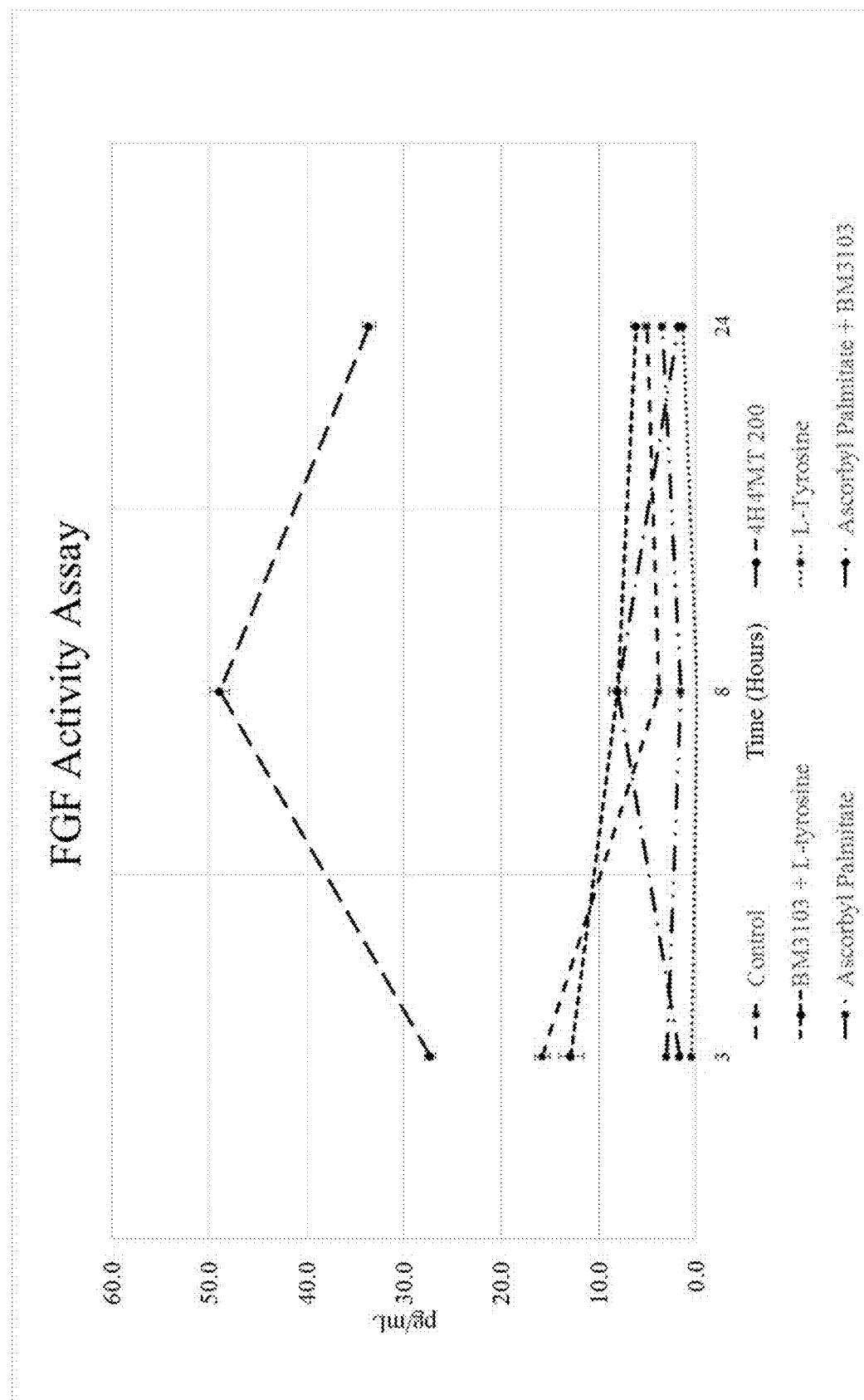
FIG. 7 is a graph of Fibroblast Growth Factor as described in Example 9.

Example 9: Fibroblast growth factor (FGF): HDFn cells were plated in a 6 well tissue culture treated plate and allowed to reach 70-80% (cells/area) confluency. A cell scraper was then used to create a "scratch" down the middle of the plate to simulate injury to the cell monolayer. Dishes were then washed with media to remove any cellular debris. Cells were then treated with Control media, FAM, AAM or combination and samples were then take at 3, 8, and 24 hrs. Samples were spun down, aliquoted and frozen until they could be assayed using an ELISA. FGF Streptavidin-HRP ELISA kit was used to determine concentration of EGF in each sample as compared to a known standard curve. Results are shown in FIG. 7.

Example 10: In Vivo Evaluation of the LCB's for Wound Healing: Twenty, 5-6 week old Balbc/J (stock #000651) male mice were transferred to Jackson Labs in vivo research laboratory in Sacramento, Calif. The mice were ear notched for identification and housed in individually and positively ventilated polycarbonate cages with HEPA filtered air. Bed-o-cob corn cob bedding was used and cages were changed every two weeks. The animal room is lighted entirely with artificial fluorescent lighting, with a controlled 12 h light/dark cycle. The normal temperature and relative humidity ranges in the animal rooms are 22 t 4° C. and 50 t 15%, respectively. The animal rooms were set to have 15 air exchanges per hour. Filtered tap water, acidified to a pH of 2.8 to 3.1, and rodent chow was provided ad libitum. Following a 5-7 days acclimation, mice were randomized by body weight into 2 cohorts of 10 mice each. On study day 0, mice were anesthetized and two full thickness excision wounds (~6 mm) were made on the dorsum (backs) of mice. One of the wounds was covered using a semi-occlusive polyurethane dressing (Tegaderm™). Dressings covered the wounds for 5 consecutive (5) days from the day of wounding (d 0). The doses of 4-hydroxy-4'-methoxytolan were based on those that promoted lesion healing in mice in previous herpes virus studies. Wound measurements were made on day 5, 7, 9 and 11. Digital images of wounds were taken of each mouse. Test agents were a viscous paste and wounds were surrounded with a saddle glued in place to eliminate cross contamination and wound closure due to contraction. Therefore, changes in wound area are due to re-epithelization. During the five days all wounds are covered with glycerin (control) or glycerin and test agent. At day 5, test agents were removed and changes in wound area were measured (as area/area %) in an effort to gauge the persistence of the compounds in the wound site. By day 5, glycerin produced 26.1% wound closure, whereas 4-hydroxy-4'-methoxytolan (2.5%) closed produced 92.8% wound closure and 5% 4-hydroxy-4'-methoxytolan produced 91.4% wound closure. Prior to statistical analysis a test for Normality was run and a Z-score computed to confirm a normally distributed area for each wound on day 1 for all mice across groups, $r^2=0.989$. Statistics are computed based One-Way ANOVA's comparing changes in wound area on day 5. All mice tolerated the treatments and all weekly clinical observations report bright, alert, responsive, and hydrated mice.

TABLE D

| Wound size reduction | | |
|---|---|---|
| Day | Average Area ($cm^2$) | Wound Area (%) Closed |
| Control Animals | | |
| 0 | 2.11 | 0 |
| 5 | 1.56 | 26.1 |
| 7 | 0.63 | 70.2 |
| 9 | 0.55 | 73.9 |
| 11 | 0.49 | 76.8 |
| 4-hydroxy-4'-methoxytolan 5% (w/v) | | |
| 0 | 1.98 | 0 |
| 5 | 0.17 | 91.4 |
| 7 | 0.08 | 100 |
| 9 | 0.00 | 100.0 |
| 11 | 0.00 | 100.0 |
| 4-hydroxy-4'-methoxytolan 2.5% (w/v) | | |
| 0 | 2.07 | 0 |
| 5 | 0.15 | 92.8 |
| 7 | 0.04 | 100 |
| 9 | 0.00 | 100.0 |
| 11 | 0.00 | 100.0 |

Example 11: Excised skin samples treated with a control or with 5% (w/v) 4-hydroxy-4'-methoxytolan. H&E staining of control treated cells revealed a keratinocyte layer of 1-2 cells thick on top of a loosely organized layer of myofibroblasts, connective tissue with a few deep sebaceous glands beginning to form. 4-hydroxy-4'-methoxytolan treated skin revealed-extensive keratinocyte proliferation with cell layers 7-8 cells thick. The dermis showed regular and proliferative myofibroblasts and connective tissue surrounding highly proliferative and prevalent sebaceous glands extending to the surface to reestablish hair follicles.

Example 12: Autophagy and Hair Re-growth in skin appendages (Hair Loss): Autophagosome-like structures have been detected by electron microscopy of hair and sebaceous glands. While the physiological relevance of autophagy in skin appendages is not well understood at present, current existing data suggests induction of autophagy may prevent hairloss through a Wnt1 dependent cell rejuvenating process where damaged cells undergo cell death and hair stem cell are stimulated to generate hair growth (Castilho R. M., et al. (2009) *mTOR mediates Wnt-induced epidermal stem cell exhaustion and aging*, Cell Stem Cell 5, 279-289; and Vishnyakova, et al. (2013) *Possible Role of Autophagy Activation in Stimulation of Regeneration*, Molecular Biology. 47(5): 692-700).

Example 13: UV Radiation damage and Anti-aging: The skin is the largest organ in the human body and is in contact with the environment. As such it is constantly subjected to damage, both from outside and from the inside, which threatens its balance and alters its appearance. This damage is often manifested as chronic low levels of inflammation. It is known for example that excessive exposure to UV is reflected by various cutaneous manifestations, such as actinic erythemas, solar elastosis, or else the premature appearance of the effects of cutaneous aging: the skin becomes loose, deeply wrinkled, rough, dry, sprinkled with hypopigmented or hyperpigmented spots and dilated vessels. These manifestations of UV exposure, which reflect profound structural changes in the cutaneous tissue, are unsightly and ugly, and many people have a tendency to want to smooth them out. TEM and IF microscopy analysis of cultured dermal fibroblasts from women of different ages revealed an impaired autophagic flux. When young dermal fibroblasts were treated with lysosomal protease inhibitors to mimic the condition of aged dermal fibroblasts the reduced autophagic activity, altered the fibroblast content of type I procollagen, hyaluronan and elastin, and caused a breakdown of collagen fibrils. Together these findings suggest that impaired autophagic induction leads to deterioration of dermal integrity and skin fragility (Tashiro K, et al. (2014) *Age-related disruption of autophagy in dermal fibroblasts modulates extracellular matrix components*, Biochem Biophys Res Commun. 443(1): 167-172).

Autophagy ensures that damaged cellular organelles and protein aggregates are degraded properly and do not accumulate causing cellular dysfunction. Enhanced autophagic activity is also seen in response to caloric restriction (CR) which has shown to prolong life expectancy.

Example 14: A 40% (w/v) solution of Hydroxypropyl-β-cyclodextrin: Solution is prepared by adding into a sterile graduated beaker 40.0 g of Hydroxypropyl-β-cyclodextrin to 70 mL of water and mixed thoroughly. Once the solution is clear QS to 100 mL. Weigh out 1.0 g of the liquid crystal compound (FAM) and transfer into a sterile glass bottle. Add 1.5 mL of ethanol to the bottle and dissolve completely. Slowly add 1 mL of cyclodextrin while stirring to ensure drug remains in solution. Add 5 mL of water while stirring to ensure drug stays in solution. Sonicate if necessary. Formulation should be a clear solution. Filter using a 0.2 um filter. The suspension is frozen below −40° C. and is lyophilized. The lyophilized cake maybe reconstituted with sterile water prior to use.

Example 15: Preparation of an injectable liquid crystal formulation FAM cyclodetrin formulation: 100 mg of a 4,4'-dihydroxytolan compound are weighed and placed in a 5 ml scintillation tube. 1.5 ml of absolute ethanol is added to the tube and shaken until the 4,4'-dihydroxytolan is completely dissolved. 5 grams of pyrogen free hydroxypropyl-β-cyclodextrin (Sigma) are weighed on an analytical scale and placed in a graduated cylinder. Water is added with shaking until the volume reaches 90 ml. The above ethanolic solution of FAM is added to the aqueous solution containing hydroxypropyl-β-cyclodextrin with stirring. Water is added to the clear solution to make the total volume 100 ml. The solution is sterile filtered through a 0.22 micron filter. The suspension is frozen below −40° C. and is lyophilized. The lyophilized cake is reconstituted with sterile water for injection prior to use.

Example 16: Preparation of Drop Solution: The solution is compounded from the ingredients; FAM-cyclodextrin 0.625 parts; saccharin sodium 0.3 parts; sorbic acid 0.1 parts; ethanol 30.0 parts; flavoring 1.0 parts; distilled water q.s. ad 100.0 parts. The FAM-cyclodextrin complex and the flavoring are dissolved in the ethanol, and the sorbic acid and the saccharin are dissolved in the distilled water. The two solutions are uniformly admixed with each other, and the mixed solution is filtered until free from suspended matter: 1 ml of the filtrate contains the FAM and is an oral dosage unit composition with effective therapeutic action.

Example 17: Preparation of Micronized Drug and Drug Suspensions: 16 grams of micronized FAM is milled with a 4 inch mill size and compressed nitrogen gas/compressed air (dew point >40° C.) as milling gas. The material is manually fed into the hopper and placed on top of the feed tray. The material is drawn into a confined, circular chamber by way of a pressurized milling gas. The powder becomes suspended in a high velocity stream in the milling chamber. Particle size distribution is measured on a particle size analyzer. The milling conditions are then adjusted to give material with an acceptable micron size.

Example 18: An FAM or AAM Modulator-Cyclodextrin Complex gel: 100 mg of an FAM is weighed and placed in a sterile test tube. The FAM is dissolved in 2-3 ml of purified absolute ethanol. 50 ml of a 10-50% (w/v) solution of hydroxypropyl-β-cyclodextrin (other cyclodextrans may also be used based on the need for water absorption such as α-cyclodextrins, 7-cyclodextrins and certain modified β-cyclodextrins) is prepared in a 150 ml sterile beaker and the solution is heated to 70-80° C. while stirring on a hot plate. The ethanolic solution of FAM is slowly added to the beaker with stirring. At this stage the AAM may be added from 1-25% (w/v). The addition of the FAM will start the gel-sol transition and if desired a gelling molecule such as sodium pectate dissolved in deionized water can be added to further enhance gelation. Other gel enhancers include the monovalent or divalent cation FAM or AAM salts which will form ionic cross linkages to enhance gel formation.

The use of cations can be selected based on the desire to increase or decrease solubility in water. In order to enhance the gelation process an FAM or its magnesium dimer is added to alginate copolymers during mixing and the M/G ratio is adjusted to create stabile FAM:$Mg^{2+}$:Alginate biodegradable sheets. The FAM cation interacts through hydrogen bonding with the pocket created by the G form alginate copolymers. All ratios can be adjusted to optimize FAM concentration and polymerization. When necessary in addition to $Mg^{2+}$ other ions such as $Ca^{2+}$, $K^+$ or $Zn^{2+}$ may be added further enhance the gelling process.

Alginates G, M or G/M copolymers through the addition of divalent cations such as calcium form calcium alginate sheets. These sheets can be created in a sterile environment and are non-irritating, non-sensitizing and biodegradable. This makes liquid crystal FAM molecules ideal molecules to promote alginate gelation, polymerization, control copolymer block structure and alter acetylation to influence the physicochemical and rheological characteristics of the polymer. In addition to adjusting the molecular mass of the individual alginate monomers the selected FAM's may also alter gel viscosity.

A variety of polymeric sugar molecules that when combined with liquid crystal FAM and AAM molecules described in this application can create unique hydrogels, alginates and drug delivery systems that can be used in creating novel wound care products. Examples include but are not limited to chitosan, hyaluronic acid, pectin, heparin, alginate, chondroitin sulfate A, D &E, PEG (polyethylene glycol), PLA (polylactic acid) and polymers thereof and polyphosphazene.

In certain instances an additional FAM or AAM may be added to any of the above formulations to improve solubility, adjust pH, balance cation or anion concentration, improve adherence to the skin, increase or decrease solubility in water, create a concentration gradient, improve gel-sol transition, increase or decrease electrical conductivity, increase or decrease capacitance, adjust overall resistance or impedance.

The formulations described in this patent are liquid crystal hormetic substances that have been shown to induce autophagy in a dose dependent fashion for the treatment of a variety of diseases and medical conditions, including increased wound closure and re-epitheliazation.

Example 19: An FAM or AAM Modulator-Alginate Complex: One gram of sodium alginate is dissolved in deionized water in a 500 mL beaker and to that is added if desired a selected AAM (1-25% w/v) is added while mixing. To this solution is added a therapeutically effective amount of an FAM that was previously dissolved in ethanol to a desired concentration 1-50% (w/v) and if necessary the addition of a monovalent or divalent cationic salt is added until the gel has reached desired consistency. For salts of FAM's the previous step is not required. The liquid crystal nature of the FAM molecules creates unique co-block polymers that associate through hydrogen, electrostatic and ionic bonding. This solution can then be used to coat woven cotton or other fibers to create alginate bandages. This same solution can also be used to create biodegradable sheets, films, beads or gels.

The foregoing description of the various aspects and embodiments of the present invention has been presented for purposes of illustration and description. It is not intended to be exhaustive of all embodiments or to limit the invention to the specific aspects disclosed. Obvious modifications or variations are possible in light of the above teachings and such modifications and variations may well fall within the scope of the invention as determined by the appended claims when interpreted in accordance with the breadth to which they are fairly, legally and equitably entitled.

What is claimed is:

1. A composition comprising a first autophagy modulating compound dispersed in a hydrogel, wherein the first autophagy modulating compound has the structure (I):

(I)

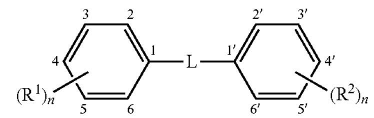

wherein L is a linker comprising —C≡C—;

$R^1$ and $R^2$ are independently substituents at any available position of the phenyl rings;

m and n are, independently, 0, 1, 2, or 3, representing the number of substituents on the rings, respectively, and at least one of m or n must be ≥1;

wherein each of $R^1$ and $R^2$ is independently selected from:

$R^5$, wherein $R^5$ is selected from $(C_1\text{-}C_6)$alkyl, $(C_2\text{-}C_6)$alkenyl, or $(C_2\text{-}C_6)$alkynyl, optionally substituted with 1 to 3 substituents selected from —OH, —SH, -halo, —$NH_2$, or $NO_2$;

$YR^6$, wherein Y is O, S, or NH; and $R^6$ is selected from H or $R^5$;

$ZR^5$, wherein Z is —N(C═O)— or —O(C═O)—;

halo;

$NO_2$;

$SO_3Na$;

azide; and glycosides;

and salts thereof;

with the proviso that the first autophagy modulating compound is not resveratrol or 4,4'-(ethyne-1,2-diyl) diphenol (TOLECINE, also known as 4,4'-dihydroxytolan).

2. The composition of claim 1, wherein the hydrogel is a liquid crystalline hydrogel formed in part by the first autophagy modulating compound.

3. The composition of claim 1, wherein the hydrogel is an alginate.

4. The composition of claim 1, further comprising a cyclodextrin.

5. The composition of claim 4, wherein the cyclodextrin is present in a ratio of the first autophagy modulating compound:cyclodextrin of from about 1:1 to about 1:10.

6. The composition of claim 4, wherein the cyclodextrin comprises hydroxypropyl-β-cyclodextrin.

7. The composition of claim 1, wherein the first autophagy modulating compound is a hydroxylated tolan, having from 1 to 4 hydroxyl substituents.

8. The composition of claim 1, wherein the first autophagy modulating compound is selected from the group consisting of: 2,4,4'-trihydroxytolan; 4,3',5'-trihydroxytolan; 2,2',4,4'-tetrahydroxytolan; 3,3',5,5'-tetrahydroxytolan; 4-hydroxy-4'-(trifluoro)methyltolan; 4,4'-dihydroxy-3-methoxytolan; 2,4,4'-trihydroxytolan-beta-D-glucoside; and 4-hydroxy-4'-methoxytolan.

9. The composition of claim 1, wherein the first autophagy modulating compound is 4-hydroxy-4'-methoxytolan or 2,4,4'-trimethoxytolan.

10. The composition of claim 1, further comprising an auxiliary autophagy modulating compound.

11. The composition of claim 10, wherein the auxiliary autophagy modulating compound is selected from the group consisting of: substituted or unsubstituted parabenzoquinone, substituted or unsubstituted orthobenzoquinone, substituted or unsubstituted anthraquinone, an amino acid, an acidic monosaccharide, and a vitamin or a salt thereof.

12. The composition of claim 11, wherein the vitamin is an oxygen-containing vitamin or an isoprenoid-containing vitamin.

13. The composition of claim 1, wherein the $(C_1-C_6)$alkyl is methyl, -n-propyl, isopropyl, -n-butyl, sec-butyl, isobutyl, or tert-butyl.

14. A composition comprising a first autophagy modulating compound in a complex with ascorbate and a cation comprising magnesium or zinc, wherein the first autophagy modulating compound has the structure (I):

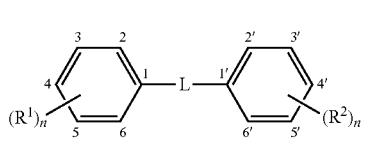

wherein L is a linker comprising —C≡C—;
$R^1$ and $R^2$ are independently substituents at any available position of the phenyl rings;
m and n are, independently, 0, 1, 2, or 3, representing the number of substituents on the rings, respectively, and at least one of m or n must be ≥1;
wherein each of $R^1$ and $R^2$ is independently selected from:
  $R^5$, wherein $R^5$ is selected from $(C_1-C_6)$alkyl, $(C_2-C_6)$alkenyl, or $(C_2-C_6)$alkynyl, optionally substituted with 1 to 3 substituents selected from —OH, —SH, -halo, —NH$_2$, or NO$_2$;
  YR$^6$, wherein Y is O, S, or NH; and $R^6$ is selected from H or $R^5$;
  ZR$^5$, wherein Z is —N(C═O)— or —O(C═O)—;
  halo;
  NO$_2$;
  SO$_3$Na;
  azide; and
  glycosides;
and salts thereof;
with the proviso that the first autophagy modulating compound is not resveratrol or 4,4'-(ethyne-1,2-diyl)diphenol (TOLECINE, also known as 4,4'-dihydroxytolan).

15. The composition of claim 14, wherein the complex comprises Mg-ascorbate-4-hydroxy-4'-methoxytolan.

16. The composition of claim 14, wherein the complex comprises Zn-ascorbate-4-hydroxy-4'-methoxytolan.

17. The composition of claim 14, wherein the first autophagy modulating compound is a hydroxylated tolan, having from 1 to 4 hydroxyl substituents.

18. The composition of claim 14, wherein the first autophagy modulating compound is selected from the group consisting of: 2,4,4'-trihydroxytolan; 4,3',5'-trihydroxytolan; 2,2',4,4'-tetrahydroxytolan; 3,3',5,5'-tetrahydroxytolan; 4-hydroxy-4'-(trifluoro)methyltolan; 4,4'-dihydroxy-3-methoxytolan; 2,4,4'-trihydroxytolan-beta-D-glucoside; and 4-hydroxy-4'-methoxytolan.

19. The composition of claim 14, wherein the first autophagy modulating compound is 4-hydroxy-4'-methoxytolan or 2,4,4'-trimethoxytolan.

20. The composition of claim 14, further comprising an auxiliary autophagy modulating compound.

21. A composition comprising a first autophagy modulating compound dispersed in a hydrogel, wherein the first autophagy modulating compound is selected from the group consisting of: 2,4,4'-trihydroxytolan; 4,3',5'-trihydroxytolan; 2,2',4,4'-tetrahydroxytolan; 3,3',5,5'-tetrahydroxytolan; 4-hydroxy-4'-(trifluoro)methyltolan; 4,4'-dihydroxy-3-methoxytolan; 2,4,4'-trihydroxytolan-beta-D-glucoside; and 4-hydroxy-4'-methoxytolan.

22. The composition of claim 21, wherein the first autophagy modulating compound is 4-hydroxy-4'-methoxytolan or 2,4,4'-trimethoxytolan.

23. A composition comprising a first autophagy modulating compound in a complex with ascorbate and a cation, wherein the first autophagy modulating compound is 4-hydroxy-4'-methoxytolan or 2,4,4'-trimethoxytolan.

* * * * *